(12) United States Patent
Ehlers et al.

(10) Patent No.: US 12,274,248 B2
(45) Date of Patent: Apr. 15, 2025

(54) HETERORHABDITIS BACTERIOPHORA WITH ENHANCED SHELF-LIFE

(71) Applicant: e-nema Gesellschaft für Biotechnologie und Biologischen Pflanzenschutz MBH, Schwentinental (DE)

(72) Inventors: Ralf-Udo Ehlers, Schwentinental (DE); Carlos Molina, Schwentinental (DE); Bart Vandenbossche, Schwentinental (DE); Olaf Strauch, Schwentinental (DE)

(73) Assignee: e-nema Gesellschaft für Biotechnologie und Biologischen Pflanzenschutz mbH, Schwentinental (DE)

( * ) Notice: Subject to any disclaimer, the term of this patent is extended or adjusted under 35 U.S.C. 154(b) by 923 days.

(21) Appl. No.: 17/263,435

(22) PCT Filed: Jul. 15, 2019

(86) PCT No.: PCT/EP2019/069000
§ 371 (c)(1),
(2) Date: Jan. 26, 2021

(87) PCT Pub. No.: WO2020/020687
PCT Pub. Date: Jan. 30, 2020

(65) Prior Publication Data
US 2022/0192167 A1    Jun. 23, 2022

(30) Foreign Application Priority Data
Jul. 27, 2018   (EP) ..................................... 18186046

(51) Int. Cl.
*A01K 67/64* (2025.01)
*A01N 63/12* (2020.01)

(52) U.S. Cl.
CPC .............. *A01K 67/64* (2025.01); *A01N 63/12* (2020.01); *A01K 2227/703* (2013.01); *A01K 2267/02* (2013.01)

(58) Field of Classification Search
CPC .......... A01K 67/0336; A01K 2227/703; A01K 2267/02; A01K 2217/00; A01N 63/12
See application file for complete search history.

(56) References Cited

PUBLICATIONS

Sumaya et al. "Applying inbreeding, hybridization and mutagenesis to improve oxidative stress tolerance and longevity of the entomopathogenic nematode *Heterorhabditis bacteriophora*." Journal of invertebrate pathology 151 (2018): 50-58 (Year: 2018).*

Bai et al., "A Lover and a Fighter: The Genome Sequence of an Entomopathogenic Nematode *Heterorhabditis bacteriophora*", *PLOS One*, vol. 8, No. 7, pp. 3-4, Jul. 2013.
Bai et al., "Transcriptomic Analysis of the Entomopathogenic Nematode *Heterorhabditis bacteriophora* TTO1", *BMC Genomics*, 20090430 BioMed Central, vol. 10, No. 1, pp. 205, 2009.
Cobb, "Estimating the Population of the Soil, with Specific Reference to the Sugarbeet and Root-gall Nemas, Heterodera Schachtii Schmidt and Heterodera Radicicola (Greet) Muller, and with a description of *Tylencholaimus aequalis* n. sp. USDA" *Agricultural Technical Circle*, vol. 1, pp. 1-47, 1918.
Database EMBL [online] "HTAB-aad54g02.b1 Heterorhabditis_bacteriophora_HTAB2_EST Heterorhabditis Bacteriophora cDNA, mRNA Sequence", Sep. 2007.
Ehlers et al., "Genetic Selection for Heat Tolerance and Low Temperature Activity of the Entomopthogenic Nematode-bacterium Complex Heterorhabditis Bacteriophora-Photorhabdus Luminescens", *BioControl*, 20051001 Kluwer Academic Publishers, Do, vol. 50, No. 5, pp. 699-716, 2005.
Ehlers, "Mass Production of Entomopathogenic Nematodes for Plant Protection", *Applied Microbiology and Biotechnology*, vol. 56, pp. 623-633, 2001.
Elshire et al., "A Robust, Simple Genotyping-by-Sequencing (GBS) Approach for High Diversity Species", *PLOS One 20110101 Public Library of Science*, vol. 6, No. 5, pp. e19379.
Glazer et al., "Overview of the Research Focused on the Application of Entomopathogenic Nematodes in Europe", Jan. 2016, https://www.researchgate.net/profile/Apostolos_Kapranas/publication/312525774_Overview_of_the_research_focused_on_the_application_of_entomopathogenic_nematodes_in_Europe/links/5880a23945851503b6edd3d4/Overview-of-the-research-focused-on-the-application-of-entomopathogenic-nematodes-in-Europe.pdf.
Grewal et al., "Dauer Juvenile Longevity and Stress Tolerance in Natural Populations of Entomopathogenic Nematodes: is There a Relationship?" *International Journal for Parasitology*, vol. 32, pp. 717-725, 2002.
Grewal et al., "Nematodes as Biocontrol Agents" *CAB International*, article "Formulation and Quality Control of Entomopathogenic Nematodes", pp. 79-90, 2005.
Hills et al., "A Method of Evaluating Post Planting Insecticide Treatments for Control of Western Corn Rootworm Larvae", *Journal of Economic Entomology*, vol. 64, pp. 764-765, 1971.
Inoue et al., "The DM Domain Transcription Factor MAB-3 Regulates Male Hypersensitivity to Oxidative Stress in Caenorhabditis Elegans", *Molecular and Cellular Biology*, vol. 30, No. 14, pp. 3453-3459, May 2010.

(Continued)

*Primary Examiner* — Jeremy C Flinders
*Assistant Examiner* — Alexander W Nicol
(74) *Attorney, Agent, or Firm* — Jordan IP Law, LLC

(57) ABSTRACT

Entomopathogenic nematode *Heterorhabditis bacteriophora* having an enhanced longevity, comprising a first locus comprising a single nucleotide polymorphism at position 75 of the nucleotide sequence SC00004647 as depicted in SEQ ID NO: 5, in which C is substituted by T; and/or a second locus comprising a single nucleotide polymorphism at position 54 of the nucleotide sequence SC00006203 as depicted in SEQ ID NO: 7, in which C is substituted by T.

7 Claims, 20 Drawing Sheets
Specification includes a Sequence Listing.

(56) References Cited

PUBLICATIONS

Iraki et al., "Isolation and Characterization of Two Entomopathogenic Nematode Strains, *Heterhabditis indica* (Nematoda, Rhabditida), from the West Bank, Palestinian Territories", *Journal of Applied Entomology*, vol. 124, pp. 375-380, 2000.

Kiss et al., "Western Corn Rootworm: Ecology and Management", *CAB International, article*, "Western Corn Rootworm (*Diabrotica Virgifera Virgifera LeConte*) and the Crop Rotation System in Europe", pp. 189-220, 2005.

Krysan et al., "Systematics of the Virgifera Species Group of Diabrotica (*Coleoptera: Chrysomelidae: Galerucinae*)", *Entomography*, vol. 5, pp. 375-484, 1987.

Long et al., "Influence of Temperature on the Infectivity of Entomopathogenic Nematodes (*Steinernema* and *Heterohabditis* spp.) to Larvae and Pupae of the Vine Weevil Otiorhynchus sulcatus (*Coleoptera: Curculionidae*", *Nematology*, vol. 2, pp. 309-317, 2000.

Mukuka et al., "Improvement of Heat and Desiccation Tolerance in Heterorhabditis bacteriophora Through Cross-breeding of Tolerant Strains and Successive Genetic Selection", *BioControl, 20100227 Kluwer Academic Publishers, Do*, vol. 55, No. 4, pp. 511-521.

Mukuka et al., "Variability in Desiccation Tolerance Among Different Strains of the Entomopathogenic Nematode *Heterohabditis bacteriophora*. Communications", *Agricultural and Applied Biological Sciences*, vol. 73, pp. 669-672, 2010.

Nanette Hope et al., "Applying Inbreeding, Hybridization and Mutagenesis to Improve Oxidative Stress Tolerance and Longevity of the Entomopthogenic Nematode *Heterorhabditis bacteriophora*", *Journal of Invertebrate Pathology*, vol. 151, pp. 50-58, Nov. 2017.

Poinar, "Description and Biology of a New Insect Parasitic Rhabditoid, *Heterorhabditis bacteriophora* N. Gen., N. Sp. (Rhabditida; Heterorhabditidae N. Fam.", *Nematologica*, vol. 21, pp. 463-470, 1975.

Regeai et al., "Novel Primers for the Amplification of Nuclear DNA Introns in the Entomopathogenic Nematode *Heterorhabditis bacteriophora* and Their Cross-amplification in Several Other Heterorhabditis species", *Molecular Ecology Resources*, vol. 9, pp. 421-424, 2009.

Shapiro-Ilan et al., "Viability and Virulence of Entomopathogenic Nematodes Exposed to Ultraviolet Radiation", *Journal of Nematology*, vol. 47, pp. 184-189, 2015.

Strauch et al., "Genetic Improvement of the Desiccation Tolerance of the Entomopathogenic Nematode *Heterorhabditis bacteriophora* Through Selective Breeding", *Biological Control*, vol. 31, pp. 218-226, 2004.

Sumaya et al., "Applying Inbreeding, Hybridization, and Mutagenesis to Improve Oxidative Stress Tolerance and Longevity of the Entomopathogenic Nematode *Heterorhabditis bacteriophora*", *Journal of Invertebrate Pathology* (In Revision), 2017.

Sumaya et al., "Phenotyping Dauer Juvenile Oxidative Stress Tolerance, Longevity and Persistence within Wild Type and Inbred Lines of the Entomopathogenic Nematode *Heterorhabditis bacteriophora*", *Nematology*, vol. 51, pp. 50-58, 2017.

Toepfer et al., "Comparative Assessment of the Efficacy of Entomopathogenic Nematode Species at Reducing Western Corn Rootworm Larvae and Root Damage in Maize", *Journal of Applied Entomology*, vol. 132, pp. 337-348, 2008.

Toepfer et al., "Controlling Western Corn Rootworm Larvae with Entomopathogenic Nematodes: Effect of Application Techniques on Plant-scale Efficacy", *Journal of Applied Entomology*, vol. 134, pp. 467-480, 2010.

Toepfer et al., "Screening of Entomopathogenic Nematodes for Virulence Against the Invasive Western Corn Rootworm, *Diabrotica Virgifera Virgifera (Coleoptera: Chrysomelidae)* in Europe", *Bulletin of Entomological Research*, vol. 95, pp. 473-482, 2005.

Vadnal et al., "Identification of Candidate Infection Genes from the Model Entomopathogenic Nematode *Heterorhabditis bacteriophora*", *BMC Genomics*, vol. 18, pp. 8, 2017.

Y et al., "The daf-2 Gene Network for Longevity Regulates Oxidative Stress Resistance and Mn-Superoxide Dismutase Gene Expression in Caenorhabditis Elegans", *The Faseb Journal, Federation of American Societies for Experimental Biology*, vol. 13, No. 11, pp. 1385-1393, Aug. 1999.

Guo et al., "Efficacy of Entomopathogenic Steinernema and Heterorhabditis Nematodes Against White Grubs (*Coleoptera: Scarabaeidae*) in Peanut Fields", Journal of Economic Entomology, vol. 106, No. 3. pp. 1112-1117. 2013.

Johnigk et al., "Endotokia matricida in hermaphrodites of *Heterorhabditis* spp. and the effect of the food supply", Nematology, vol. 1, pp. 717-726. 1999.

\* cited by examiner

```
                    ┌─────────────────────────┐
                    │  Wild type strains and  │
                    │      inbred lines       │
                    └────────────┬────────────┘
                       ┌─────────┴──────────┐
                       ▼                    ▼
          ┌──────────────────────┐  ┌──────────────────────┐
          │ Longevity estimation │  │ Virulence estimation │
          │  by oxidative stress │  │  LD50 against mealworm│
          │    (70 Mm H2O2)      │  │                      │
          └──────────┬───────────┘  └──────────┬───────────┘
                     └──────────┬──────────────┘
                                ▼
                   Rating of strains with
                   good and bad DJ-
                   longevity and virulence
```

Flow:

- Wild type strains and inbred lines → Longevity estimation by oxidative stress (70 Mm $H_2O_2$); Virulence estimation $LD_{50}$ against mealworm
- → Rating of strains with good and bad DJ-longevity and virulence
- → Selection of two contrasting materials in DJ-longevity for genetic analysis
  - → Genetic crossing → RILs derivation → Genotyping of WT strains and RILs → QTL and association Analysis → Development of PCR-Markers from SNPs with significance for DJ-longevity and virulence
- → Selection of a prominent strain based on genotypic and phenotypic data
  - → Long living and high virulent HU2 strain
    - → Generation of the HU2-IL1 line → Field and semi-field Test against Western corn rootworm → Selection for persistence in soil → DJ-Longevity test in formulation

SEQUENCE LISTING

<160> NUMBER OF SEQ ID NOS: 16

<210> SEQ ID NO 1
<211> LENGTH: 164
<212> TYPE: DNA
<213> ORGANISM: Heterorhabditis bacteriophora

```
<220> FEATURE:
<223> OTHER INFORMATION: SC00003427

<400> SEQUENCE: 1
ttatcaagta aataaagttc gtctattttt attaagattt tctcactaaa gtgataagta    60
tgttgkagtt cttgattagt attaattaac agcgattaaa tgccagagag gcaataaacg   120
ctgtgtaaac ccacattaat ttagctttttt ctattcacag attc                   164

<210> SEQ ID NO 2
<211> LENGTH: 178
<212> TYPE: DNA
<213> ORGANISM: Heterorhabditis bacteriophora
<220> FEATURE:
<223> OTHER INFORMATION: SC00004141

<400> SEQUENCE: 2
tacatacttg cattaaatgg aacaaagtgc tcatcaatgt gcatttagta tttacatcta    60
tgtgtatgaa atgtgwcatc tgtatattgt gcgaacttaa caaagaaaga cttattgagg   120 tcattttat atacatggtg tccacgataa aaggacctat ttgacaagtt ttataact     178

<210> SEQ ID NO 3
<211> LENGTH: 164
<212> TYPE: DNA
<213> ORGANISM: Heterorhabditis bacteriophora
<220> FEATURE:
<223> OTHER INFORMATION: SC00004554

<400> SEQUENCE: 3
aattaaaccg cagatgaccg agccaggggt gagttttcg gtgcacttcg atgtgagttt    60
gaagactgcg agrgatgtaa gtttactggt gagttttcct ttatattttt tttcagtact   120
ctcctgagcc gaggcgtttg cctcagtgct cttttcccac ctcc                    164

<210> SEQ ID NO 4
<211> LENGTH: 180
<212> TYPE: DNA
<213> ORGANISM: Heterorhabditis bacteriophora
<220> FEATURE:
<223> OTHER INFORMATION: SC00004634

<400> SEQUENCE: 4
atcttttagg aagtacaaaa gatgtataat ttatttacta gtaataattc gccacgttct    60
tctactatcc atgttgatgt tgtcaytatg tttaagcact tgataggtat atggatacac   120
atctgagatt tcgtgtcatt tactttaccc cggttacttt tcgggctatt ttataccctt   180

<210> SEQ ID NO 5
<211> LENGTH: 164
<212> TYPE: DNA
<213> ORGANISM: Heterorhabditis bacteriophora
<220> FEATURE:
<223> OTHER INFORMATION: SC00004647

<400> SEQUENCE: 5
aacttagtaa taaaattcgt aaaaattatt ttatgcttac attcactcct atggacttct    60
acatagaagg cttcygatga gcggggaata agccctcgct gtccagtggc aatattcatc   120
gcatccagtg aacaatccct ttaatatgtg aaacttaaag ttgg                    164

<210> SEQ ID NO 6
<211> LENGTH: 232
<212> TYPE: DNA
```

```
<213> ORGANISM: Heterorhabditis bacteriophora
<220> FEATURE:
<223> OTHER INFORMATION: SC00005330

<400> SEQUENCE: 6
ctattactac tactattact attatcaagt tgagttaaat taataaaggt gaaaatattg      60
tggcattatt tttgacatgc ctgtggtttg aatcactrct ttttttatc atgatttta      120 ttctagaatg gtaccaaatt gtatagtaaa ggcgaagaac gaaaggaagc gagtatacgt    180
cggtgaagaa ttatgtgaat gtgctgatcg aagcagccta ttcttcgtat ta            232

<210> SEQ ID NO 7
<211> LENGTH: 164
<212> TYPE: DNA
<213> ORGANISM: Heterorhabditis bacteriophora
<220> FEATURE:
<223> OTHER INFORMATION: SC00006203

<400> SEQUENCE: 7
tcaccgaaat attgtggtag aagttagcgt gagaagttgg actcatatta gtgytattca    60
tcgaatggac atgggaaaac agttactcag ataactgttc ctttgccctg tgaataaggg   120
cagatttaat cttacggtta ctggtcttca tggctgaaca actt                     164

<210> SEQ ID NO 8
<211> LENGTH: 164
<212> TYPE: DNA
<213> ORGANISM: Heterorhabditis bacteriophora
<220> FEATURE:
<223> OTHER INFORMATION: SC00010093

<400> SEQUENCE: 8
gtggcgagaa gaaagaataa gtattatttg aaagatcaat atccattaat atgagtgaac    60
aattgaatag gacaatagtt aaatgataga aggtttaact caatggttaa rtttaaaaag   120
ataagggaac tacttcagac aggtcttcgg cgcacggaat cggc                     164

<210> SEQ ID NO 9
<211> LENGTH: 164
<212> TYPE: DNA
<213> ORGANISM: Heterorhabditis bacteriophora
<220> FEATURE:
<223> OTHER INFORMATION: SC00012917

<400> SEQUENCE: 9
ttgttccatt gttcaaaaac attgtaatac tgtcaactat tgcttggaac atgttctaga    60
ataatggttc attggcsatt tgccgtcatt agtaatgtta aaatagtttt aatctgtagt   120
ggatttgtgg cggacgcagt ggttgatgca tcagaattgt tcca                     164

<210> SEQ ID NO 10
<211> LENGTH: 318
<212> TYPE: DNA
<213> ORGANISM: Heterorhabditis bacteriophora
<220> FEATURE:
<223> OTHER INFORMATION: EN-Hb_oxid-11688

<400> SEQUENCE: 10
gcttcatggt tttagccata caatcgatga tgccattata ggcattcatg gtttgtagtc    60
tagccttgac tgtgtccagc ggatgtccaa cgagaaggcc tgctcctcct aacatattaa   120
aggtcatagc cgatctcgcc cgccccattt tctcagcgta ataatcaat cgaactacga    180 gaggtcaacc aaacggctgs actgcttatt gacagttttg ctgttagcgt tctcgtattt   240
```

|  |  |
| --- | --- |
| tatatttgca cctcattata ttttagtttg tctaattaaa tatatgaact aattgataaa | 300 |
| taaataggtt cttacttc | 318 |

<210> SEQ ID NO 11
<211> LENGTH: 376
<212> TYPE: DNA
<213> ORGANISM: Heterorhabditis bacteriophora
<220> FEATURE:
<223> OTHER INFORMATION: EN-Hb_oxid-26008

<400> SEQUENCE: 11

|  |  |
| --- | --- |
| caaaaattcc gatcaacata ctttatacat tttatcgtta tgaagtcatt tattcattga | 60 |
| ctgagaaaaa tataagtgaa gagccactaa ttaatcgata tataagtagc tacaagattg | 120 |
| atttttaata ctattgtaaa taataattag ttaaatgcat tgtagcaaat taaaarctaa | 180 |
| tgatatctaa gaaaatcccg gaagaaaagg atacgaaacg gtcatctaac aacgctataa | 240 |
| taattatgca gttttaattt tcttgctatt aaaaaatcgt aacaataaca ttgatacata | 300 |
| tatatcgatt aattagtggc tcttcactta tattttctc agtcaatgaa taaatgactt | 360 |
| cataacgata aaatgt | 376 |

<210> SEQ ID NO 12
<211> LENGTH: 164
<212> TYPE: DNA
<213> ORGANISM: Heterorhabditis bacteriophora
<220> FEATURE:
<223> OTHER INFORMATION: SC00004911

<400> SEQUENCE: 12

|  |  |
| --- | --- |
| ggatcgagta aagtattaat gacttccatg tcgtggcatt gaccacttgg atgtgacaag | 60 |
| aacctcagtg ggagtctttt ctattcagca atagactgaa aataataata aayaagaaat | 120 |
| aaacacgtga tatgtgagaa ataaagaaac ttattcagac agat | 164 |

<210> SEQ ID NO 13
<211> LENGTH: 164
<212> TYPE: DNA
<213> ORGANISM: Heterorhabditis bacteriophora
<220> FEATURE:
<223> OTHER INFORMATION: SC00011215

<400> SEQUENCE: 13

|  |  |
| --- | --- |
| ctttgcttat gatacaacta ttaacactca gtctcttgaa atacatgtgc atgtacagat | 60 |
| gytataaaga cgtataatac acaataaata aaaaatagag taaacattag aacaatttta | 120 |
| tagattagaa aactatttac tgaaaaattt actggtattg atta | 164 |

<210> SEQ ID NO 14
<211> LENGTH: 164
<212> TYPE: DNA
<213> ORGANISM: Heterorhabditis bacteriophora
<220> FEATURE:
<223> OTHER INFORMATION: SC00013602

<400> SEQUENCE: 14

|  |  |
| --- | --- |
| gtgtggtcgt cattcgattt ggacacgatt gggaccctac atgcatgcga atggatgagg | 60 |
| ttaggttgtt ctctaacatt ttggcaaatt ttttcrggac aaactacata tgcaaatctt | 120 |
| ttatagacac tgttcaaaat cgctcccaaa atcaaaaatt tctc | 164 |

<210> SEQ ID NO 15

```
<211> LENGTH: 322
<212> TYPE: DNA
<213> ORGANISM: Heterorhabditis bacteriophora
<220> FEATURE:
<223> OTHER INFORMATION: EN-Hb_oxid-05173

<400> SEQUENCE: 15
tggagttacc tgccgccatt tcatatattg tcgttttaga tgcttacttg tcgcggacta      60
agggagaacc tcttggaaga caagctccgg ccoctggaag acttccaact acaccaggca     120
ggactggcaa cccttctatg aagttcactg caggaagcgg ctcacgaagc cgaaaatagc     180
aatctttaat gttttaccck caatattgat tagtattttg cttatggccc aatttctgaa     240
atgcatttta ctattgtatc atgcaataca ataatcttta atatcgattt tcatcatcag     300
agaatgaaat tattgcaacg aa                                              322

<210> SEQ ID NO 16
<211> LENGTH: 401
<212> TYPE: DNA
<213> ORGANISM: Heterorhabditis bacteriophora
<220> FEATURE:
<223> OTHER INFORMATION: EN-Hb_oxid-56985

<400> SEQUENCE: 16
gtgtggtagt tttatgtcac gagctggaag tagacagtct ttcacaagtt gatccttaac      60
aagtgtttca ttgaaatgcc ataaacctat aaaaagactt atgaattttt tctgctaact     120
aggtctccgg tttcgaatcc aatgagaacg cgataatagg ctctaatgga aacccaaaga     180
tctttcactt gatcagccac rgcatcaact aaggcttctt cgaaaggcgt ctttccagca     240
aaaccaaact ttctggctaa atatcttgca cctgcatagg attgaccaat ctgtttccca     300
tcaacctcaa ggatagggac ctgtccaaat ggcattgttg ctttatactt tggccacatg     360
tcaattggta tgcggtaatc ttcatactcc tggcctgcta g                         401
```

HETERORHABDITIS BACTERIOPHORA WITH ENHANCED SHELF-LIFE

CROSS-REFERENCE TO RELATED APPLICATIONS

This application represents the U.S. National Phase of International Application number PCT/EP2019/069000 entitled "*Heterorhabditis bacteriophora* with Enhanced Shelf-Life" filed 15 Jul. 2019, which claims benefit to European Patent Application number 18186046.1 filed 27 Jul. 2018, all of which are incorporated herein by reference.

SEQUENCE LISTING

The instant application contains a Sequence Listing which has been submitted electronically in ASCII format and is hereby incorporated by reference in its entirety. Said ASCII copy, created on Aug. 31, 2021, is named LBMR015US_SL.txt and is 7,077 bytes in size.

BACKGROUND OF THE INVENTION

The invention relates to an entomopathogenic nematode as a biocontrol agent with enhanced shelf-life and virulence. Particularly, the invention relates to *Heterorhabditis bacteriophora* (Poinar) as a biocontrol agent having an enhanced shelf-life and virulence.

*Heterorhabditis bacteriophora* (Poinar) is an entomopathogenic nematode (EPN) species with a broad diversity in infectivity. The market for biocontrol agents (BCA) is nowadays under constant growth, and nematodes are entering market niches on large scale field cultures.

The infective dauer juvenile (DJ) is the only free living stage of this entomopathogenic nematode, being the active form as biocontrol agent against insect pests. These dauer juveniles are shear-stress tolerant and can be easily applied using conventional spraying technology. Industrially, *H. bacteriophora* DJ are produced in bioreactors (monoxenic liquid culture) together with their symbiotic bacterium *Photorhabdus luminescens*. Infective DJs can be stored in liquid suspension before they are formulated in powder, transported, and applied on fields or greenhouses.

However, DJ gradually loose virulence and increase their mortality several weeks after production. As the nematode market grows, bigger production batches are required; and this increase in demand and production leads automatically to extended storage times for *H. bacteriophora*.

Further, the use of nematodes in field crops is hard a physiologic challenge for these nematodes. The strongest example is found in the control of the western corn rootworm (*Diabrotica virgifera virgigera*) in maize plantations. In Europe, DJ are applied at the sowing time (around April) and have to remain viable in the soil until the target insect larvae emerge (around May). During this time, the DJ are exposed to stresses like UV light, drought, high temperatures, and oxidative stress. Thus, the improvement of the survival (DJ-longevity) during storage and also after application is a major task for the production of *H. bacteriophora* as a biocontrol agent.

SUMMARY OF THE INVENTION

Hence, it is a first object of the present invention to provide a genetically distinct *Heterorhabditis bacteriophora* organism having an improved shelf-life and virulence. Particularly, it is a second object of the present invention to provide a genetically distinct *Heterorhabditis bacteriophora* organism having an improved shelf-life and virulence as a source of a biocontrol agent against insect pests. Specifically, it is a further object to provide a genetically distinct *Heterorhabditis bacteriophora* organism having an improved shelf-life and virulence as a biocontrol agent against the western corn rootworm (*Diabrotica virgifera virgigera*).

The invention is based on the finding of a strong correlation between oxidative stress tolerance and DJ-longevity in entomopathogenic nematode (EPN) species of *Heterorhabditis bacteriophora*. Also, genetic crosses and phenotypic selection were done in natural strains leading to an increase in survival time. A large body of sequence data comprising more than 55.000 transcripts and more than 1.100 single nucleotide polymorphisms (SNPs) from contrasting materials in virulence- and DJ-longevity have been generated and deeply analyzed. Thereafter, relevant information has been transferred into genotyping molecular markers to test the genotype-phenotype correlation. As outcome, a set of PCR-based molecular markers that show association with EPN beneficial traits (DJ-longevity and virulence) has been identified. A series of *H. bacteriophora* strains, inbred lines, and mutants has been also resulting from the virulence and DJ-longevity characterization. Among them, the HU2 strain and the HU2-IL1 have shown the most robust performance results on the control of *Dioabrotica v. virgifera* in contrast to the current commercial *H. bacteriophora* strain and compared to the chemical control agent.

Accordingly, there is claimed an entomopathogenic nematode *Heterorhabditis bacteriophora* having an enhanced longevity, comprising a first locus comprising a single nucleotide polymorphism at position 75 of the nucleotide sequence SC00004647 as depicted in SEQ ID NO: 5, in which C is substituted by T; and/or a second locus comprising a single nucleotide polymorphism at position 54 of the nucleotide sequence SC00006203 as depicted in SEQ ID NO: 7, in which C is substituted by T.

Preferably, the entomopathogenic nematode further is having a third locus comprising a single nucleotide polymorphism at position 66 of the nucleotide sequence SC00003427 as depicted in SEQ ID NO: 1, in which Tis substituted by G; and/or a fourth locus comprising a single nucleotide polymorphism at position 76 of the nucleotide sequence SC00004141 as depicted in SEQ ID NO: 2, in which A is substituted by T; and/or a fifth locus comprising a single nucleotide polymorphism at position 86 of the nucleotide sequence SC00004634 as depicted in SEQ ID NO: 4, in which Cis substituted by T; and/or a sixth locus comprising a single nucleotide polymorphism at position 98 of the nucleotide sequence SC00005330 as depicted in SEQ ID NO: 6, in which G is substituted by A; and/or a seventh locus comprising a single nucleotide polymorphism at position 77 of the nucleotide sequence SC00012917 as depicted in SEQ ID NO: 9, in which C is substituted by G; and/or an eighth locus comprising a single nucleotide polymorphism at position 200 of the nucleotide sequence EN-Hb_oxid-11688 as depicted in SEQ ID NO: 10, in which C is substituted by G; and/or a ninth locus comprising a single nucleotide polymorphism at position 176 of the nucleotide sequence EN-Hb_oxid-26008 as depicted in SEQ ID NO: 11, in which A is substituted by G.

More preferred, the entomopathogenic nematode is having a heterozygous genotype with a tenth locus comprising the nucleotide sequence SC00004911 as depicted in SEQ ID NO: 12 and an eleventh locus comprising a single nucleotide polymorphism at position 113 of the nucleotide sequence SC00004911 as depicted in SEQ ID NO: 12, in which C is substituted by T.

As a further preferred embodiment of the invention the entomopathogenic nematode is having a twelfth locus conferring an enhanced virulence, comprising a single nucleotide polymorphism at position 73 of the nucleotide sequence SC00004554 as depicted in SEQ ID NO: 3, in which G is substituted by A.

Alternatively or additionally, the entomopathogenic nematode is having a thirteenth locus conferring an enhanced virulence, comprising a single nucleotide polymorphism at position 111 of the nucleotide sequence SC00010093 as depicted in SEQ ID NO: 8, in which G is substituted by A.

Moreover, there is claimed a method of identifying at least one individual of entomopathogenic nematode *Heterorhabditis bacteriophora* associated with enhanced longevity, by determining a first locus comprising a single nucleotide polymorphism at position 75 of the nucleotide sequence SC00004647 as depicted in SEQ ID NO: 5, in which C is substituted by T; and/or a second locus comprising a single nucleotide polymorphism at position 54 of the nucleotide sequence SC00006203 as depicted in SEQ ID NO: 7, in which C is substituted by T.

Preferably the method comprises determining a third locus comprising a single nucleotide polymorphism at position 66 of the nucleotide sequence SC00003427 as depicted in SEQ ID NO: 1, in which T is substituted by G; and/or a fourth locus comprising a single nucleotide polymorphism at position 76 of the nucleotide sequence SC00004141 as depicted in SEQ ID NO: 2, in which A is substituted by T; and/or a fifth locus comprising a single nucleotide polymorphism at position 86 of the nucleotide sequence SC00004634 as depicted in SEQ ID NO: 4, in which C is substituted by T; and/or a sixth locus comprising a single nucleotide polymorphism at position 98 of the nucleotide sequence SC00005330 as depicted in SEQ ID NO: 6, in which G is substituted by A; and/or a seventh locus comprising a single nucleotide polymorphism at position 77 of the nucleotide sequence SC00012917 as depicted in SEQ ID NO: 9, in which C is substituted by G; and/or an eighth locus comprising a single nucleotide polymorphism at position 200 of the nucleotide sequence EN-Hb_oxid-11688 as depicted in SEQ ID NO: 10, in which C is substituted by G; and/or a ninth locus comprising a single nucleotide polymorphism at position 176 of the nucleotide sequence EN-Hb_oxid-26008 as depicted in SEQ ID NO: 11, in which A is substituted by G.

According to a further preferred embodiment the method includes the identification of an individual having a heterozygous genotype comprising a tenth locus comprising the nucleotide sequence SC00004911 as depicted in SEQ ID NO: 12 and an eleventh locus comprising a single nucleotide polymorphism at position 113 of the nucleotide sequence SC00004911 as depicted in SEQ ID NO: 12, in which C is substituted by T.

Also, there is claimed a method of identifying at least one individual of entomopathogenic nematode *Heterorhabditis bacteriophora* associated with enhanced virulence, by determining a twelfth locus conferring an enhanced virulence, comprising a single nucleotide polymorphism at position 73 of the nucleotide sequence SC00004554 as depicted in SEQ ID NO: 3, in which G is substituted by A or by determining a thirteenth locus conferring an enhanced virulence, comprising a single nucleotide polymorphism at position 111 of the nucleotide sequence SC00010093 as depicted in SEQ ID NO: 8, in which G is substituted by A.

Based on the above a biological control agent is provided comprising the entomopathogenic nematode having at least one of the above identified loci and/or which has been determined by the aforementioned methods.

As a preferred embodiment the biological control agent is provided comprising at least one agriculturally acceptable carrier.

Finally, according to the invention, the use of the entomopathogenic nematode having the features of the invention against true weevils (Curculionidae), scarabs (Scarabaeidae) or leaf beetles (Chrsysomelidae) is provided, wherein the use against the western corn rootworm (*Diabrotica virgifera virgifera*) is particularly preferred.

General Remarks

*Heterorhabditis bacteriophora* Poinar (Poinar 1975) is an effective biological control agent (BCA) against insect pests in economically important crops (Grewal et al., 2005). This species has a symbiotic association with the bacterium *Photorhabdus luminescens*, which is carried by the nematodes in the free-living, developmentally arrested DJ stage. *Heterorhabditis bacteriophora* is used commercially mainly for the control of several curculionid weevil larvae in soft fruit and ornamentals (Long et al., 2000), and white grubs in turf (Koppenhöfer et al., 2015). This EPN species has also large potential as BCA against the invasive maize pest western corn rootworm *Diabrotica virgifera virgifera* (Toepfer et al., 2005).

Despite several advantages offered by this species, its use in larger scale agriculture is restricted by a limited shelf-life and high sensitivity to environmental stress conditions (Strauch et al., 2004; Mukuka et al., 2010a and b). DJ of *H. bacteriophora* are industrially produced in monoxenic liquid culture in bioreactors and are stored in liquid suspension at high densities for maximum 6 weeks after production (Ehlers, 2001). For transport and storage to the end-users, DJ need to be formulated under moderate desiccation (Grewal and Peters, 2005). Additional to the stress to which EPN are exposed during production and transport, post-application stress factors such as UV-radiation, high temperatures, drought and oxidative stress, reduce the DJ-survival (Grewal et al., 2002; Strauch et al., 2004; Ehlers et al., 2005; Mukuka et al., 2010a; Sumaya et. al, 2017). Thus, improvement of DJ-longevity and virulence are priority tasks for *H. bacteriophora* as BCA.

Classical genetics have been applied in beneficial traits-improvement using the phenotypic and genetic natural variability as starting points. Cross-breeding and successive genetic selection, for instance, have evidenced a significant heat and desiccation stress-tolerance improvement in *H. bacteriophora*. For instance, Ehlers et al. (2005) increased the mean tolerated temperature of a *H. bacteriophora* hybrid strain to 39.2° C. Subsequently, Mukuka et al. (2010a, c) screened 60 *H. bacteriophora* strains from different geographical origin and reported an increase to 44.0° C. after eleven selection steps. Other traits related to EPNs such as virulence appear to have more complex genetic backgrounds due to influence of several factors such as host-finding ability, persistence, and infective-related aspects. Up to date, no correlation between stress-tolerance and virulence in EPNs has been found (Shapiro-Ilan et al. 2015).

Understanding the physiological and molecular mechanisms behind the DJ-longevity and virulence in *H. bacteriophora* should open doors in the search for molecular markers associated to these traits. Molecular markers can be applied in breeding programs where they can be used as trait predictors. Sequence data availability on this species for the design of molecular markers has only been gradually increasing during the past ten years. For instance, Bai et al. (2009) reported on the availability of 168 microsatellite loci from 157 distinct *H. bacteriophora* Expressed Sequence Tag (EST) sequences, which were generated by cDNA libraries sequencing. In a parallel work, Regeai et al. (2009) reported on the availability of 24 intron-derived markers in housekeeping and structural genes of *H. bacteriophora*. Subsequently, a primary draft sequence of the *H. bacteriophora* genome was released in 2013 by Bai and co-authors. Only until recently, Vadnal et al (2017) reported on the first published RNA-seq analysis of *H. bacteriophora* DJs, using the current genome draft as reference sequence.

In the framework of the EU Project BIOCOMES, three deep RNA-seq analyses were carried out yielding more than 55.000 de novo assembled transcripts. Additionally, SNPs were sequenced in genomic DNA using the Genotyping by Sequencing (GBS) method, yielding more than 1200 Polymorphic SNPs. Thereafter, SNP information was used to construct a low resolution linkage map, which was combined with phenotypic information to carry out a DJ-longevity QTL analysis. As final outcome, correlation analysis between genotype and phenotype data yielded twelve PCR-based SNP markers that can be used as DJ-longevity predictors. Additionally, two of these markers show also high association with DJ-virulence.

To evaluate the versatility of the inbred lines and strains identified and generated we assessed their performance on the control of the western corn rootworm or WCR (*Diabrotica virgifera virgifera* LeConte; Coleoptera: Chrysomelidae) in maize plantations. Supposed to have originated and evolved together with maize in Central America (Krysan & Smith, 1987), the WCR turned into a key pest when maize expanded to North America (Vidal et al., 2005; Toepfer et al., 2005, 2010). Followed by several introductions from the USA, WCR has rapidly spread in central Europe, becoming a significant threat to maize production principally in some countries such as Austria, Hungary, Serbia, Romania and Italy (Kiss et al., 2005a; Toepfer et al., 2010). Concerning biological control, *H. bacteriophora* has been previously appointed as a potential BCA for *D. v. virgifera* (Toepfer et al., 2005). However, post-application environmental stresses such as desiccation, UV-radiation, change in temperatures, and time-lapse without host larvae still substantially reduce the DJ-efficacy of this EPN. Thus, *H. bacteriophora* strains and inbred lines with enhanced stress-tolerance, longevity, and virulence have a great potential on the biologic control of this pest.

Two approaches were followed to achieve improved beneficial traits in *H. bacteriophora* as BCA: i) identification of strains and lines that already combine high virulence and DJ-longevity, and ii) combination of properties by genetic crossing and selection. In this context, the wild type (WT) strain named HU2 has been identified to combine high-virulence and DJ-longevity. This WT strain was evaluated individually, and was used to generate hybrid pools after crossing with WT strains with high virulence. The hybrid pools derived from the crosses have also shown improved performance. Extensive virulence and DJ-longevity characterization starting from laboratory assays up to field trials in central Europe confirm the phenotypic improvement as BCA against *D. v. virgifera*.

BRIEF DESCRIPTION OF THE FIGURES

Main experimental steps and milestones for the generation and evaluation of natural strains and hybrids are depicted in the accompanying drawings, wherein:

FIG. 1 shows the main experimental steps carried out towards the selection and testing of *Heteorhabditis bacteriophora* materials with improved performance. Processes depicted in dotted lines denote support information derived from stress-characterization and molecular analyses.

FIG. 2B shows the Mean $LD_{50}$ per *Tenebrio molitor* larvae from DJs along a set of *Heterorhabditis bacteriophora* WT strains and inbred lines. Host mortality was assessed after 7 days of exposure to DJs at 25° C. Error bars: SD of four replicates. Different letters on the error bars indicate significant differences (Conover-Iman test with Bonferroni correction at $P<0.0001$)

FIG. 15 shows the efficacy of nematodes and chemical insecticide (Cypermethrin) treatments in reduction of *Diabrotica v. virgifera* in artificially-infested field trials in Hungarian sites on 2016. All treatments are compared against the untreated control parcels. Emerging adults were counted upon application of 100 eggs per plant. Nematodes from the EN01 and HU2 strains were applied at 2×109 DJs ha-1. Error bars: SD from two fields.

FIG. 16 shows the efficacy (%) of DJ and chemical insecticide (Cypermethrin 12 kg ha-1) treatments in reduction the plant root damage (IWOA scale) in artificially-infested field trials in Hungarian sites in 2016. All treatments are compared against the untreated control parcels. Nematodes from the EN01 and HU2 strains were applied at 2×109 DJs ha-1. Error bars: SD from two fields.

DETAILED DESCRIPTION OF THE INVENTION

Nematodes Growth in Monoxenic Cultures

Figure 2A:
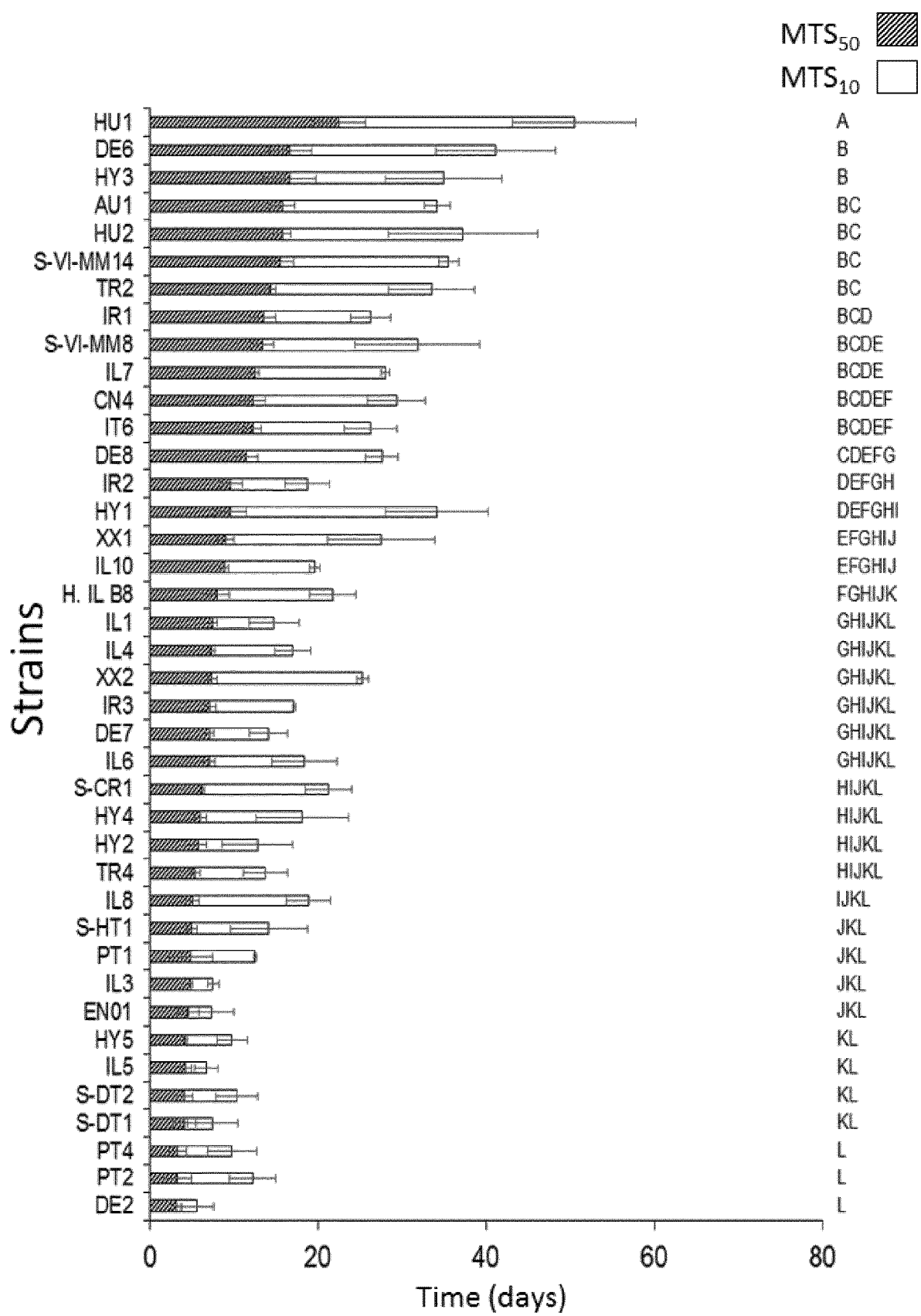
FIG. 2A shows the mean time survived by 50% ($MTS_{50}$) and best 10% ($MTS_{10}$) of DJ populations from *Heterorhabditis bacteriophora* strains and lines stored at 25° C. under oxidative stress (70 mM $H_2O_2$). The MTS for each line was calculated by fitting a cumulative distribution curve. Error bars: standard deviation (SD) from three independent biological replicates (each with three replicates). Different letters denote significant differences (Tukey's HSD test at $P \leq 0.05$). Further information is available under Sumaya et al. (2017).

Starting from a collection of 40 *H. bacteriophora* strains that were collected in several parts of the world and that have been worked in the lab in previous research, the isolates were propagated in Nematode Gelrite Media (NGG; gelrite 3.0 gl-1, peptone 2.50 gl-1, NaCl 51 mM, $CaCl_2$) *$H_2O$ 1 mM, $MgSO_4$*$7H_2O$ 1 mM, $KH_2PO_4$ 1 mM, cholesterol 12 µM) pre-coated with pre-cultured *Photorhabdus luminescens* at a density of $2 \times 10^9$ cells $ml^{-1}$ in a semi-solid NGG matrix (NGG, 1.5 $gl^{-1}$ gelrite). After DJ-recovery and completion of one life-cycle (~7 days), mature hermaphrodites (*Endotokia matricida* stage) were washed-off from the NGG plates and re-suspended in Ringer's solution (NaCl 9 $gl^{-1}$, KCl 4.42 $gl^{-1}$, $CaCl_2 \times 2$ $H_2O$ 0.37 $gl^{-1}$, $NaHCO_3$ 0.2 $gl^{-1}$) until the majority of DJ were released. Thereafter, DJ were cleaned via cotton trap and vacuum-filtering with a 10 µm sieve. Clean DJ were stored in culture flasks In Ringer's solution until used for characterization.

Oxidative Stress Assays to Predict DJ-Longevity in Strains and Inbred Lines

Dauer Juveniles from the *H. bacteriophora* natural strains were subjected to oxidative stress assays according to Sumaya et al. (2017). DJ-populations from each line (~1,000 individuals) were disposed in 24-cell well plates in a final volume of 400 µl of Ringer's solution in three randomized technical replicates. Thereafter, 15 µl of 1.94 M $H_2O_2$ were added to each cell-well to obtain a final $H_2O_2$ concentration of 70 mM. DJ-mortality over time was assessed by periodically (~every second day) surveying 20 µl aliquots for dead and alive individuals in each replicate. The percentage of DJ-mortality was used to determine the $MTS_{50}$ of the DJ-population for each line. The $MTS_{50}$ was determined from a fitted cumulative normal distribution by using the Probit analysis of the XLSTAT (https://www.xlstat.com/de/) software. Oxidative stress assays were repeated starting from different DJ growth batches

Virulence Estimation of the Natural Strains

Mealworms (*Tenebrio molitor*) were used as hosts for the virulence characterization of *H. bacteriophora* WT materials. *Tenebrio molitor* larvae were obtained from Futterinsektenfarm Schulz (Eschach-Holzhausen, Germany). For laboratory virulence bioassays, 40 *T. molitor* larvae were placed into Petri dishes (150 mm) filled with 150 g of sand adjusted to 8.5% water content. Nematode suspension volumes of 1.0 ml (Ringer's solution) from each strain and line containing 80, 200, 400, 800 and 2000 DJs ml-1 were inoculated in the middle of the Petri dishes and incubated at 25° C. for 7 days. Infection by DJs was checked with the luminometer LUMAT LB 9501 (Berthold GmbH, Germany). The mean mortality by nematode infection of *T. molitor* was compared among all strains. Mortality data was used to calculate the lethal dose of DJs required to kill 50% of the insect larvae per assay ($LD_{50}$). The $LD_{50}$ was calculated by fitting the observed data to saturated curves, which were compared with the saturation curve through minimising the chi-square ($chi^2$) fitting to the nearest value to zero. The insect mortality was calculated through the formula:

$$mortality = a(1 - \ln(-bx)) + c$$

Where:
a=total number of insects
b=slope of the fitted model
x=number of DJs per insect
c=control mortality The data were compared with the saturation curve through minimizing the chi-square ($Chi^2$) fitting to a value nearest to cero (0). The values obtained were analyzed for normality with the Shapiro-Wilk test at P≤0.05. In case of not-normal-distribution, log transformation was used. For normal distributed data ANOVA and Tukey's test for multiple comparisons were done. For non-normal distributed data the Kruskal-Wallis test with post hoc Conover-Iman test for multiple comparisons were used. The Bonferroni test was performed for correction of significant differences. Standard deviation of $LD_{50}$ was calculated according to the formula:

$$SD = \sqrt{(\text{infected rate} \times \text{non-infected} \times \text{total insects}) \div (\text{total insects})}$$

Results on Variability in DJ-Longevity and Virulence Among *H. bactariophora* Strains

Differences in $MTS_{50}$ Among *H. bacteriophora* Strains

The highly positive correlation between oxidative stress tolerance and DJ-longevity, as well as a comprehensive overview of this characterization has been published by Sumaya et al. (2017). We determined a high variability and significant differences (F=36.62; df=39; P≤0.0001) on mean time survived by 50% of DJ populations ($MTS_{50}$) along the 40 tested *H. bacteriophora* strains. The $MTS_{50}$ in DJ-populations under oxidative stress (70 mM $H_2O_2$) ranged from 3.2±0.65 up to 22.46±3.18 days. This measurement was highly correlated (R=0.87, P≤0.001) with survival bioassays carried out under control conditions (0.0 mM $H_2O_2$, 25° C.). Natural isolates from central Europe and Australia were found among the longest surviving materials. Among them is found the strain HU2, which also showed high virulence in parallel tests. An overview of the determined $MTS_{50}$ under oxidative stress is presented in FIG. 2A.

Figure 2B:
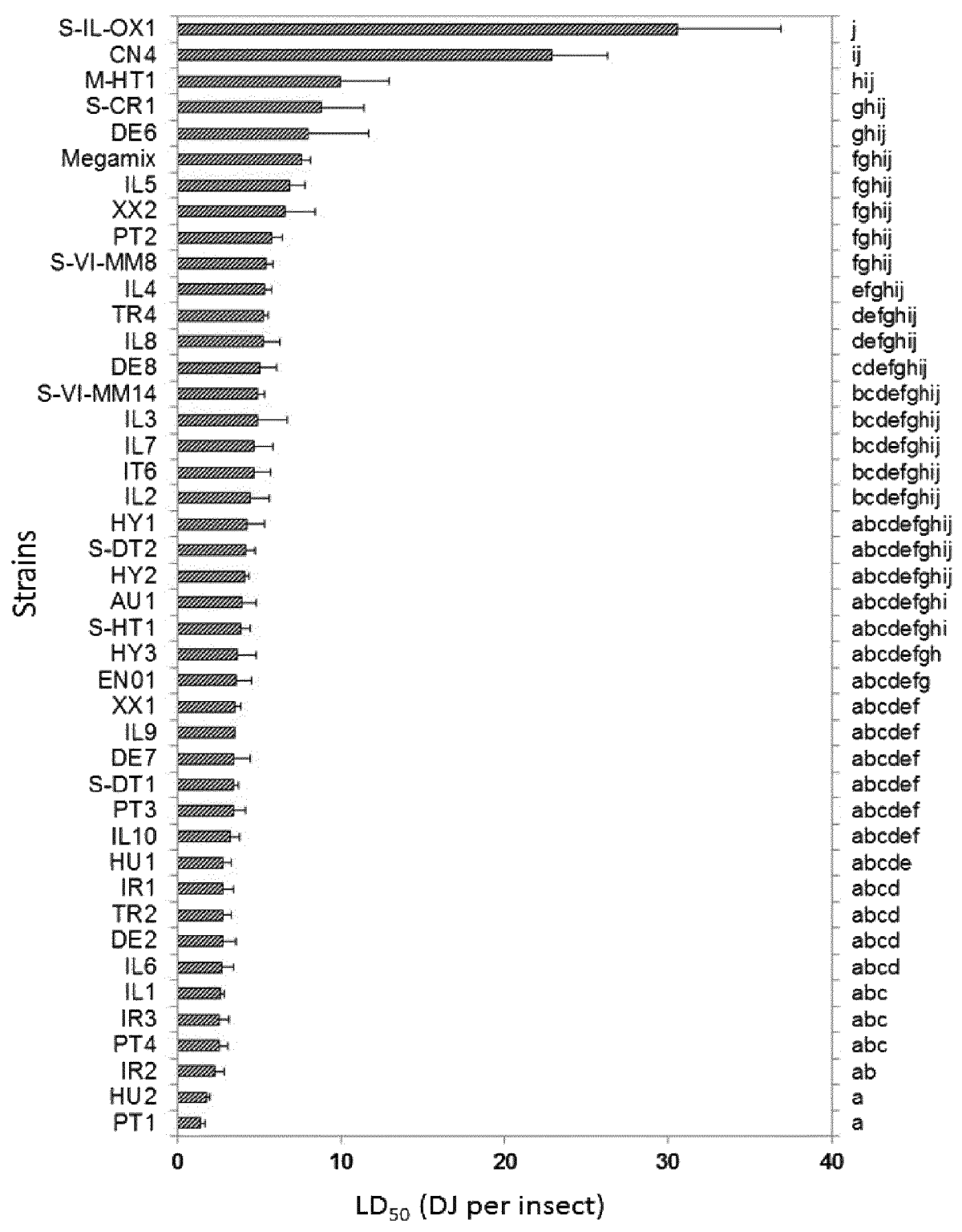

Concerning virulence, all WT strains and inbred lines were able to infect *T molitor* larvae, and significant differences were found among the $LD_{50}$ values (K=120.55; df=42; P≤0.0001). The $LD_{50}$ of the tested materials ranged from 1.4 to 30.5 DJs per insect. The isolate PT1, was the most virulent strain against *T. molitor* larvae with a $LD_{50}$ of 1.4±0.33, followed by the isolate HU2 ($LD_{50}$=1.8±0.23). The current commercial strain (EN01) showed a relatively high virulence level ($LD_{50}$=3.6±0.91). An overview of the $LD_{50}$ in all strains and inbred lines is depicted in FIG. 2B. Although the $LD_{50}$ of the current commercial strain EN01 does not present significant differences with the most virulent isolate, this suggests that still higher virulence could be reached by breeding or selection procedures. Thus, new isolates with lower $LD_{50}$ values and better performance in other important traits (stress-resistance and DJ-longevity) can be as well potential candidates for commercial production.

Selection of Two Contrasting Materials for Subsequent Genetic Analysis

Figure 3:
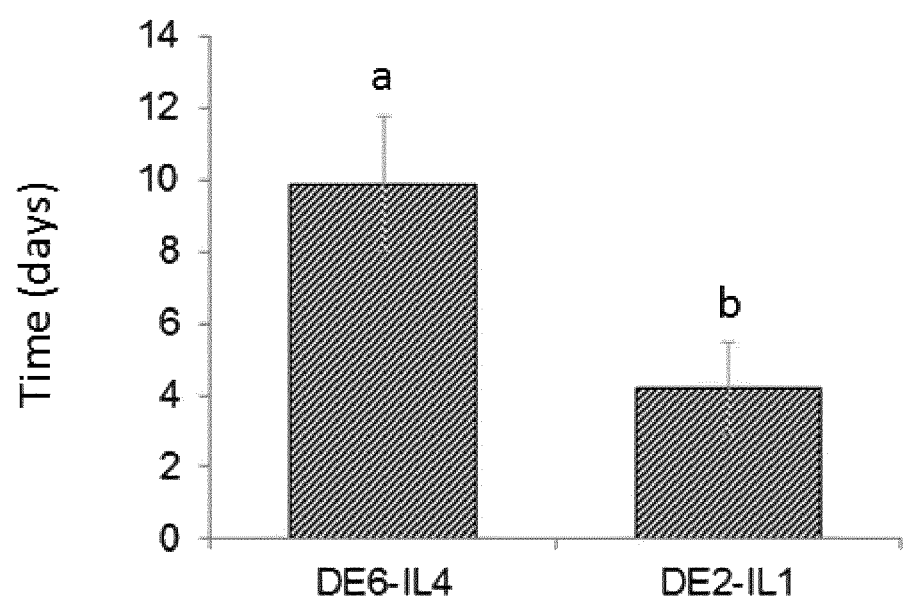
FIG. 3 shows the mean time survived by 50% ($MTS_{50}$) of DJ-populations from the contrasting lines DE6-IL4 (high survival) and DE2-IL1 (low survival). Both inbred lines were derived after 8 self-fecundation cycles. Error bars: SD from three independent trials. Different letters denote significant differences (Tukey's HSD test at $P \leq 0.05$).

Genetic analysis is crucial for the generation of molecular markers for marker-assisted breeding. In this framework we choose two strains with contrasting properties for subsequent genetic linkage and QTL analysis: i) DE2-IL1 (Short DJ-longevity, high virulence), and DE6-IL4 (large DJ-longevity, low virulence). Both strains originated respectively inbred lines after more than 8 self-fecundation cycles. The DJ-longevity phenotype of both inbred lines was confirmed by $MTS_{50}$ estimation under oxidative stress (70 mM $H_2O_2$) as shown in FIG. 3

Crossing *H. bacetriophora* Homozygous Lines to Make Genetic Analyses in Recombinant Inbred Lines (RILs)

Methods

Genetic Crossing Between Contrasting Lines

Genetic crosses were carried out with inbred lines. A description of the parental inbred lines and progeny is deposited in Table 1. All crosses were done following the report of Iraki and co-authors (2000). As outcome, sets of highly homozygous recombinant inbred lines (RILs) were obtained from each cross.

TABLE 1

*H. bacteriophora* inbred lines used for additional genetic crosses

| Cross name | Parent 1 | Phenotype | Parent 2 | Phenotype | Outcome |
|---|---|---|---|---|---|
| D2D6 | DE2-IL1 | low DJ-longevty High virulence | DE6-IL4 | high DJ-longevty low virulence | RILs |

Results on Derivation of Progenies Out of Genetic Crosses

After genetic crossing, single progeny individuals were self-fertilized for more than 8 generations ($>F_8$) to produce recombinant inbred lines (hereafter, D2D6 RILs). These lines were chosen to be extensively genotyped by high throughput sequencing using the genotyping by sequencing (GBS) approach. All RILs were also characterized for DJ-longevity. Subsequently, genotype and phenotype were correlated by QTL and association analysis.

Figure 4:
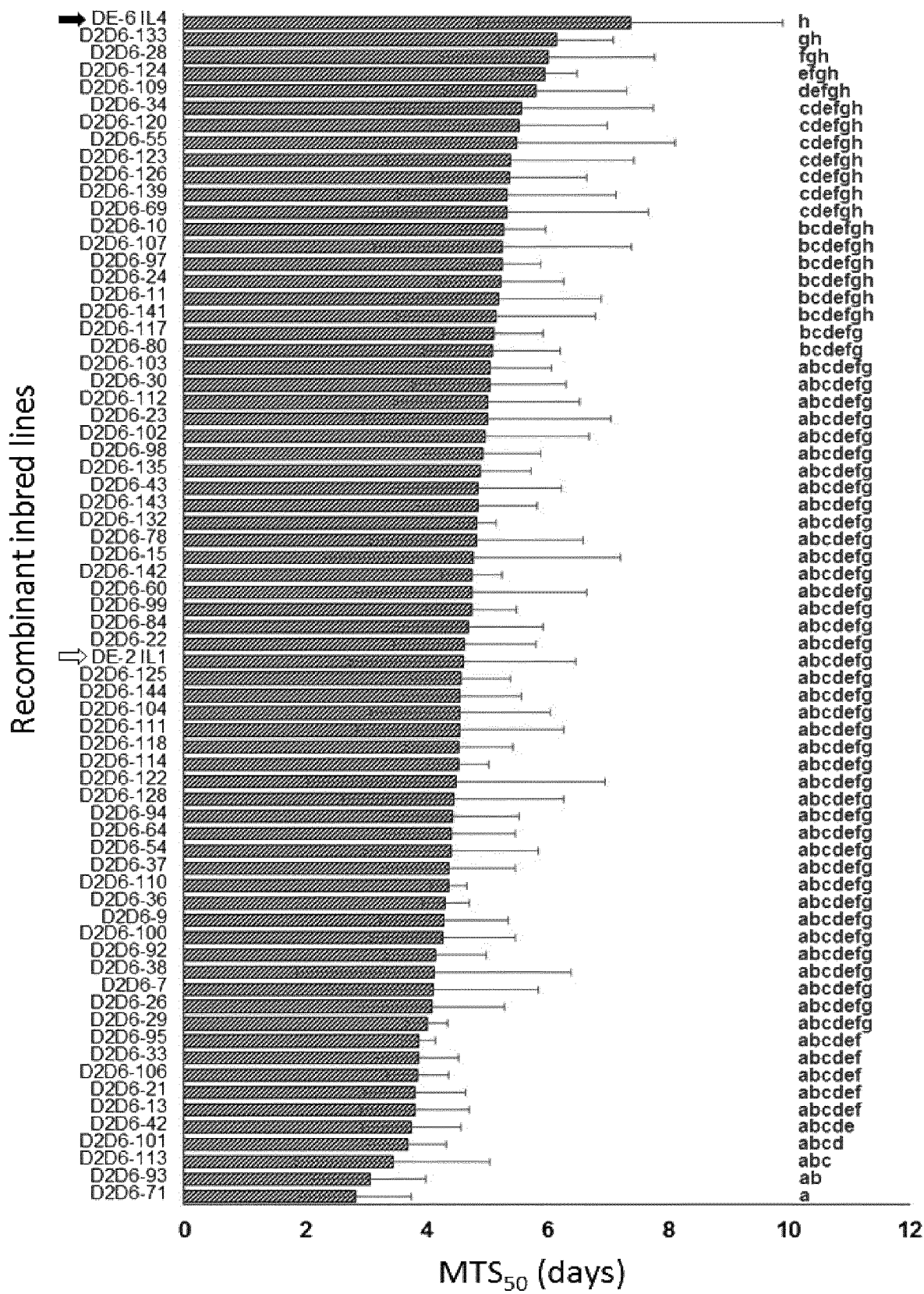
FIG. 4 shows the mean Time Survived by 50% ($MTS_{50}$) of DJ populations from D2D6-RILs and parental lines under oxidative stress assays. Two assays were conducted along 30 days. DJs of each line were treated with 70 mM $H_2O_2$ at 25° C. in three randomized replicates and counted for live and dead nematodes over time. The gray bars represent the two contrasting parents, DE6-IL4 and DE2-IL1. Error bars: SD. Letters at the right indicate significant differences among lines (Tukey's HSD test at $P \leq 0.05$).

Variability in Oxidative Stress Survival and Desiccation Tolerance Along D2D6 RILs Phenotypic data for QTL and association analysis was generated by calculating the $MTS_{50}$ under 70 mM $H_2O_2$ of each RIL derived from the D2D6 cross. The DJs of the stress tolerant parent line (DE6-IL4) survived the longest time on the set ($MTS_{50}=7.9\pm1.3$ days) whereas lower $MTS_{50}$ value ($5.1\pm1.1$ days) was determined for DE2-IL1, however not the lowest among all lines. The RIL D2D6-42 survived the shortest time among all lines ($MTS_{50}=3.7$ days). Interestingly, several lines had a shorter $MTS_{50}$ compared to that of the parental DE2-IL4 population. Differences in $MTS_{50}$ among lines resulted significant ($F=8.55$; $df=51$; $P\leq0.0001$) considering lines with $MTS_{50}$ values in both trials. An overview of the RILs survival along the parental lines is shown in FIG. 4.

Evaluating the Genetic Diversity of *H. bacteriophora* Strains and RILs Methods

Genome-Wide Genotyping by Sequencing (GBS)

Parallel to the phenotypic analysis, a subset of 28 D2D6 RILs, 11 wild type *H. bacteriophora* strains, and 6 WT inbred ILs were analyzed by GBS as described by Elshire et al. (2011). The materials selected for the analysis were chosen according to their DJ-longevity (contrasting material Table 2). All *H. bacteriophora* lines and strains chosen for GBS were propagated in NGG media and harvested as described above. Clean DJs were used for DNA extraction with the peqGOLD Tissue DNA Mini Kit (PeqLab, Germany), according to the manufacturer's instructions. All sequencing steps were carried out by the company LGC Genomics GmbH (Berlin, Germany) according the GBS standard protocol.

TABLE 2

Set of *H. bacteriophora* materials selected for GBS. For each material, its DJ-longevity under oxidative stress is depicted. Within each subset, contrasting materials are included. Materials with three different genetic backgrounds were analysed: WT strains, WT inbred lines, RILs, and selected cross-progenies

| Type | Code | Longevity 25° C./70 mM $H_2O_2$ |
|---|---|---|
| WT Strains | HY3 | High |
| | AU1 | High |
| | DE6 | High |
| | HU1 | High |
| | HU2 | High |
| | DE2 | low |
| | PT1 | low |
| | PT2 | low |
| | PT4 | low |
| | EN01 | low |
| | PT3 | low |
| WT Inbred lines | AU1-IL1 | high |
| | HU2-IL1 | high |
| | DE6-IL4 | high |
| | PT1-IL1 | low |
| | IL3 | low |
| | DE2-IL1 | low |
| RILs | D2D6-133 | high |
| | D2D6-24 | high |
| | D2D6-124 | high |
| | D2D6-125 | high |
| | D2D6-126 | high |
| | D2D6-135 | high |
| | D2D6-109 | high |
| | D2D6-99 | high |
| | D2D6-10 | high |
| | D2D6-84 | high |
| | D2D6-143 | high |
| | D2D6-144 | high |
| | D2D6-104 | high |
| | D2D6-114 | high |
| | D2D6-113 | low |
| | D2D6-111 | low |
| | D2D6-95 | low |
| | D2D6-128 | low |
| | D2D6-78 | low |
| | D2D6-71 | low |
| | D2D6-22 | low |
| | D2D6-21 | low |
| | D2D6-54 | low |
| | D2D6-93 | low |
| | D2D6-122 | low |
| | D2D6-94 | low |
| | D2D6-123A | low |
| | D2D6-123B | low |
| Selected progenies | HU2-IL1 × PT1-IL1-Vir | (very) high |
| | HU2-IL1 × PT1-IL1-LL + Vir | (very) high |
| | HU2-IL1 × PT1-IL1 | high |

In Silico Analysis of GBS Data and Genotype-Phenotype Correlation Analysis

The finality of the GBS analysis is to find polymorphisms in large numbers among the tested materials. The targeted polymorphisms are single nucleotide substitutions in the genetic code (SNPs). After sequencing, GBS clusters harboring SNPs among the analyzed strains and lines were filtered according to the allele frequencies (reduction of minor SNP alleles) and variant call files (VCF) were generated. The obtained VCF were used to test the correlation between the lines SNP-genotype and existing longevity phenotype information using the software Tassel 5.0 (http://www.maizegenetics.net/tassel). SNPs with association to a specific longevity-related trait were filtered out after analyzing natural strains and RILs in separate runs. As a complementary approach, GBS clusters showing polymor phisms along the sequenced RILs were filtered and used for linkage analysis with the software package Joinmap 4.1 (https://www.kyazma.nl) with the Kosambi genetic mapping function with a minimum LOD score (logarithm [base 10] of odds) of 2.0. For QTL analysis, the linkage map generated by joinmap 4.1 was combined with RILs phenotypic data using the PlabQTL software (https://plant-breeding.uni-hohenheim.de/software.html). PlabQTL was run including test for additive and dominance effects (no test for residuals). GBS clusters flanking QTL were selected for further analyses.

With this approach, a total of 1.075 SNPs were analyzed using the Tassel 5.0 software. Phenotypic data from the DJ-survival ($MTS_{50}$ and $MTS_{10}$) of 17 strains and inbred lines was combined with the respective SNP alleles. Phenotype information has been published by Sumaya et al. (2017). Survival time from four treatments was considered: i) 25° C.—control, 25° C.—oxidative stress, 7° C.—control, and 7° C.—oxidative stress. After data analysis, association to at least one of the traits was shown by five markers. Marker details and associations are depicted in Table 3.

TABLE 3

GBS-clusters showing SNPs with association to DJ-longevity related traits in *Heterorhabditis bacteriophora* natural strains and inbred lines. For each SNP, associated traits are depicted along their P-value. Homology hits with previously sequenced RNA-seq transcripts and contigs of the *H. bacteriophora* current genome draft are shown.

| | | Trait | | BLAST homology hits | |
| --- | --- | --- | --- | --- | --- |
| Marker | Parameter | Conditions | p-value | RNA-seq transcripts | *H. bacteriophora* genome draft |
| SC00002607 | $MTS_{50}$ | 25° C. - 70 mM $H_2O_2$ | 2.78E−05 | EN-Hb__oxid-51278 | contig1336 |
| | $MTS_{10}$ | 25° C. - 70 mM $H_2O_2$ | 7.62E−04 | EN-Hb__oxid-51278 | contig1336 |
| SC00003550 | $MTS_{50}$ | 25° C. - 70 mM $H_2O_2$ | 6.69E−06 | | |
| | $MTS_{10}$ | 25° C. - 70 mM $H_2O_2$ | 1.32E−04 | | |
| SC00004013 | $MTS_{50}$ | 7° C. - 70 mM $H_2O_2$ | 4.24E−04 | | |
| | $MTS_{10}$ | 7° C. - 70 mM $H_2O_2$ | 8.31E−04 | | |
| SC00004647 | $MTS_{50}$ | 25° C. - 70 mM $H_2O_2$ | 2.78E−05 | | contig1265 |
| | $MTS_{10}$ | 25° C. - 70 mM $H_2O_2$ | 7.62E−04 | | contig1265 |
| SC00006203 | $MTS_{50}$ | 25° C. - 70 mM $H_2O_2$ | 2.78E−05 | | contig1190 |
| | $MTS_{10}$ | 25° C. - 70 mM $H_2O_2$ | 7.62E−04 | | contig1190 |

Results on Finding SNPs with Correlation with Longevity and Virulence

Genotyping by Sequencing (GBS) in *H. bacetriophora* Strains and Lines

After GBS sequencing, Illumina paired end-sequencing yielded a total of 80.000 GBS clusters (64 bp sequence stretches). After filtering out minor SNP alleles, 1.126 clusters resulted polymorphic either in natural strains or in RILs. Further on, BLAST analyses against the public repositories yielded 380 clusters with high homology to the latest version of the *H. bacteriophora* genome draft. Additionally, 230 clusters presented high homology to the NCBI (nr) database. For Further analyses, variant call files (VCF) were generated for two categories of sequenced individuals: i) natural strains and inbred lines, ii) RILs and parental inbred lines.

Correlation Analyses Combining Phenotype and GBS Data from Strains

The phenotype and genotype information from the previously analysed *H. bacteriophora* strains and inbred lines was combined by association analysis. SNP variant calls from wild type lines and strains were analyzed under an allele frequency threshold of 0.05 for the minor SNP allele.

QTL Analysis in D2D6 RILs Using GBS Alleles

Figure 5:
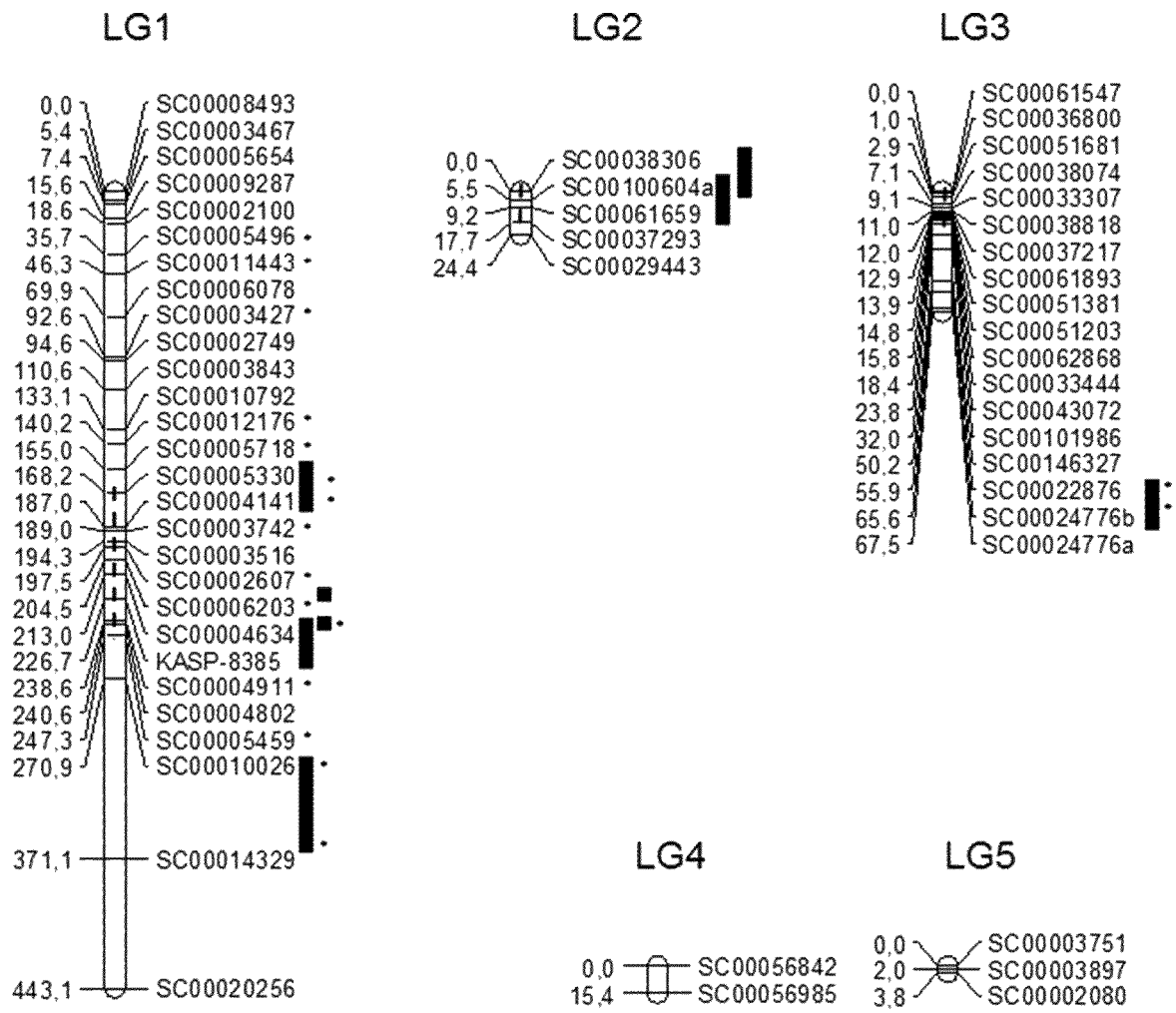
FIG. 5 shows linkage groups obtained from polymorphic SNPs analyzed in 28 RILs from the D2D6 RILs along their parental lines. Five major linkage groups were determined comprising ~550 cM. Seven QTL were identified using data from one desiccation and two oxidative stress trials independently (colour bars). Six of the seven QTL were found mainly in three linkage groups regions (red dashed lines). GBS clusters selected for design of PCR markers are denoted with a star.
Figure 6:
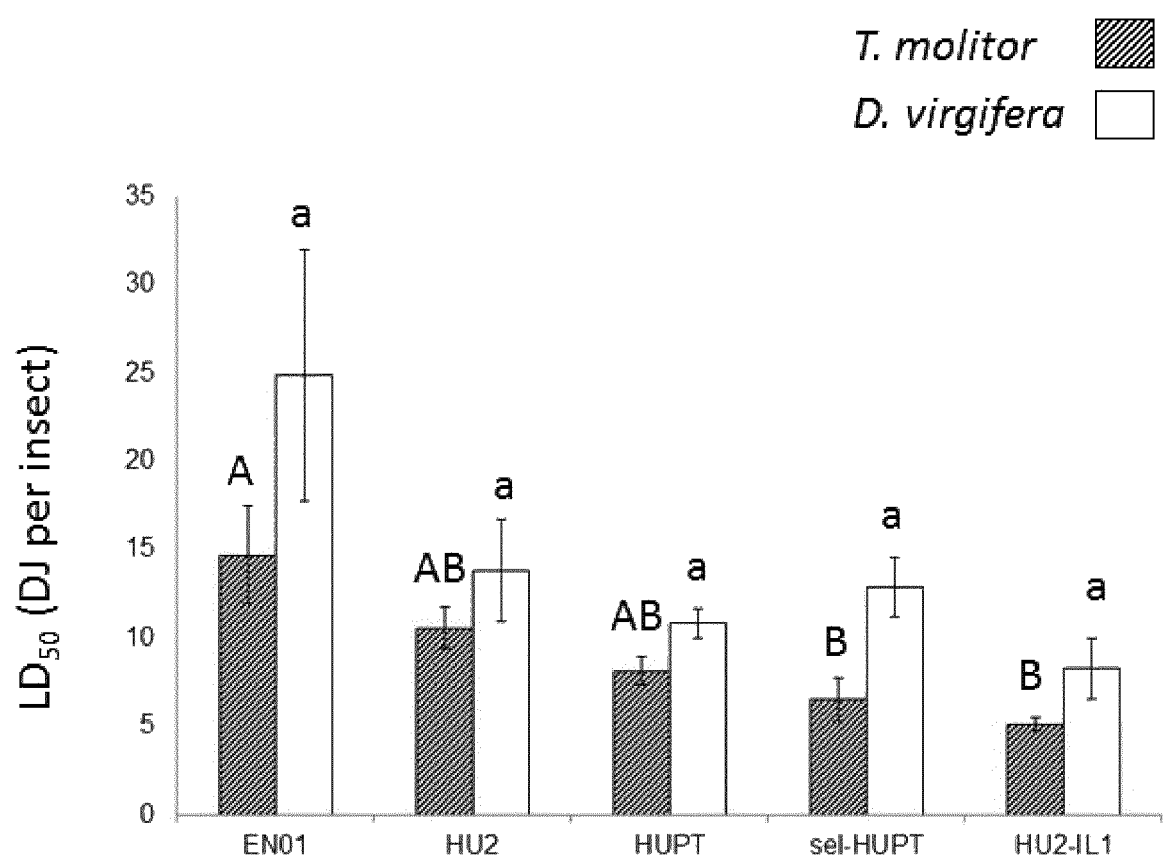
FIG. 6 depicts the main $LD_{50}$ of the *Heterorhabditis bacteriophora* commercial strain EN01 along promissory materials characterized within BIOCOMES WP2 (HU2, HUPT, sel-HUPT and HU2-IL1). Host larvae: *Tenebrio molitor* (dark bars) and *Diabrotica virgifera virgifera* L3 larvae (white bars). $LD_{50}$ was assessed after seven days of exposure at 25° C. Error bars: SEM of ten replicates for (*T. molitor*) and four replicates (*D. v. virgifera*). Different letters (uppercase for *T. molitor*, lowercase for *D. v. virgifera*) indicate significant differences (Tukey's HSD test at $P \leq 0.05$).

A QTL analysis was carried out using SNPs recorded for the 28 D2D6-RILs analyzed by GBS aside the parent lines DE2-IL1 and DE6-IL4. Genotype data was combined with RILs phenotype data described in the previous sections (DJs $MTS_{50}$ under oxidative stress). Additionally, desiccation tolerance data from the same RILs was included. For linkage analysis, 321 SNPs for the parental and the RILs were chosen. After filtering for all SNP minor alleles, 63 SNPs were used for the construction of a linkage map using the Joinmap software. A low resolution linkage map with five major linkage groups was obtained including 53 SNPs. The developed genetic map covered 553 centimorgan (cM). Thereafter, phenotype and genotype were correlated by QTL analysis. The phenotypic data from three different oxidative trials and one desiccation trial (each consisting of three technical replicates) was used independently for the QTL calculation. Seven QTL with profile LOD score above 2.0 were determined in three linkage groups. A graphic display of the linkage groups and the main QTL is depicted in FIG. 5. Basic QTL parameters are deposited in Table 4. SNPs in the vicinity of the QTL were later chosen for the design of PCR-base genotyping markers.

TABLE 4

Oxidative stress- (MTS$_{50}$) and desiccation-tolerance (Survival %) QTL detected in *Heterorhabditis bacteriophora* linkage groups determined using polymorphic SNPs. For each QTL, the left and right markers are depicted along with the total LOD score of the QTL. Positive additive effects indicate DE6-IL4 as strong parent. Negative additive effects indicate DE6-IL4 as weak parent, for the given loci.

| Trait-trial | LG | Position | Left Marker | Right Marker | LOD | Additive effect |
|---|---|---|---|---|---|---|
| MTS$_{50}$-H$_2$O$_2$-2 | 1 | 187 | SC00005330 | SC00004141 | 2.51 | 3.75 |
| MTS$_{50}$ H$_2$O$_2$-2 | 1 | 213 | SC00004634 | En_Oxid-8385 | 2.04 | −2.01 |
| MTS$_{50}$ H$_2$O$_2$-2 | 1 | 314 | SC01010026 | SC00014329 | 3.19 | −4.47 |
| MTS$_{50}$ H$_2$O$_2$-1 | 2 | 6 | SC01100604 | SC00061659 | 5.36 | 0.70 |
| MTS$_{50}$ H$_2$O$_2$-1 | 3 | 59 | SC00022876 | SC00024776 | 7.52 | −0.69 |
| MTS$_{50}$ H$_2$O$_2$-Avg | 2 | 0 | SC00038306 | SC00100604 | 1.76 | 0.56 |
| Desiccation-1 | 1 | 207 | SC00006203 | SC00004634 | 5.02 | 8.60 |

Transfer of Information from Genome-Wide SNP Analysis into PCR-Based Markers

The GBS analysis was done with a limited number of *H. bacteriophora* strains and RILs. The next step of the research was to transfer this information to design PCR-based SNP markers and to test all 40 WT strains from the nematode collection. Once all strains and RILs were genotyped, the correlation between genotype, DJ-longevity and Virulence was tested to select KASP markers with the most predictive power.

Methods

KASP Assays

Sequence information from GBS was analyzed to be converted into PCR-based markers for genotyping assays. A set of 30 candidate SNPs derived from the QTL and Association analyses described above was chosen for the SNP detection assays by PCR. Additionally SNPs were filtered of RNA-seq assays done in parallel (Table 5). The technique known as KASP (Kompetitive Allele Specific PCR) was chosen for this purpose. For KASP markers primers design, all pre-selected sequences were send to the commercial partner LGC genomics (UK). KASP-PCR amplifications were done starting from 2-3 µl DNA (10-15 ng) of each genotyped nematode material using the markers (primers) by following the PCR-profile: 94° C.-15 min; 10 cycles of 94° C.-20 sec, 61° C.-1 min (0.6° C. drop each cycle); and 30 cycles of 94° C.-20 sec, 55° C.-1 min. Resulting signals were analysed with the StepOne software (genotyping mode) of Applied Biosystems for allele discrimination. For each genotyping round, KASP assays with no DNA were used as negative controls.

Results on SNP Genotyping

KASP Genotyping in RILs and WT Strains

Out of a total of 30 KASP markers (Table 5), 23 markers where polymorphic in the 40 wild type strains. To validate the KASP results, the GBS genotypic data of the 28 D2D6-RILs and their parents was compared in 5 randomly selected KASP markers. A total of 140 data points were compared between GBS and KASP assays. From GBS clusters registered as homozygous, 94 out of 94 KASP readings were consistent with the expected genotype. In 11 cases where the GBS genotype for the given RILs was regarded as heterozygous, the KASP genotype was registered as homozygous for one of the parental alleles. In summary, 90% concordance was observed for all amplified SNPs. However, the proportion of heterozygous RILs is negligible when it is considered marker by marker.

TABLE 5

Overview of designed KASP markers for the genotyping of *Heterorhabditis bacteriophora* strains and inbred lines. Allele variants with the specific fluorophore are provided along with sequence source of the SNP.

| Marker Name | SNP source | Allele FAM | Allele HEX |
|---|---|---|---|
| SC00002607 | GBS | G | T |
| SC00003427 | | G | T |
| SC00003742 | | G | A |
| SC00004554 | | G | A |
| SC00004647 | | C | T |
| SC00004911 | | T | C |
| SC00005459 | | C | T |
| SC00005496 | | A | T |
| SC00005718 | | A | T |
| SC00006203 | | C | T |
| SC00006291 | | T | G |
| SC00010093 | | A | G |
| SC00010669 | | C | G |
| SC00011215 | | T | C |
| SC00011443 | | C | T |
| SC00012176 | | G | A |
| SC00012917 | | G | C |
| SC00013602 | | G | A |
| EN-Hb_oxid-05173 | RNA-seq | G | T |
| EN-Hb_oxid-08385 | | C | G |
| EN-Hb_oxid-11688 | | G | C |
| EN-Hb_oxid-26008 | | G | A |
| EN-Hb_oxid-41943 | | C | T |
| EN-Hb_oxid-45902 | | G | C |
| EN-Hb_oxid-48911 | | G | A |
| EN-Hb_oxid-51540 | | T | C |
| EN-Hb_oxid-56842 | | A | G |
| EN-Hb_oxid-56985 | | G | A |
| EN-Hb_oxid-58060 | | C | T |
| EN-Hb_oxid-58700 | | C | T |

Correlation Between KASPs Genotypes with DJ-Survival and DJ-Virulence

The genotypes derived from all the KASP markers were analyzed for significant phenotypic differences in survival (MTS$_{50}$) along 50 D2D6-RILs and 40 WT strains and inbred lines via ANOVA. For the D2D6 RILs, the genotypic data was combined with the $MTS_{50}$ of the RILs under oxidative stress from two experimental trials and desiccation the survival. For wild type strains and inbred lines, the genotypic data was combined with the $MTS_{50}$ under two temperatures (25° C. and 7° C.), and two conditions (0.0 and 70 mM $H_2O_2$) published by Sumaya et al (2017). Concerning virulence, the $LD_{50}$ (number of DJs to needed to kill 50% of a host population) of the WT-strains against mealworm (Tenebrio molitor) was used. Among the 40 wild type strains and inbred lines, twelve markers showed correlation between the genotype and at least one the $MTS_{50}$ parameters measured. Two of this markers (SC00004554 and SC00010093) showed also high correlation with the $LD_{50}$ against T. molitor. A detailed overview of the significant markers for the 40 wild type strains and inbred lines is given in Table 6.

SC00006203, SC00005330, SC00004141 and SC00004634 were found in the vicinity of longevity-related QTL as described above (Table 4). Moreover, markers that combined correlation with virulence and DJ-longevity (SC00004554 and SC00010093) were as well polymorphic between HU2 and EN01. Considering the overall SNP genotype of 28 KASP markers analyzed, HU2 haplotype was only shared with it sister isolate HU1, which is also possess large DJ-longevity. The KASP genotypes of the subset of markers showing highest association with DJ-longevity and virulence including their genotype, along with four additional polymorphic markers extracted from relevant transcripts and QTL vicinity, is shown in Table 7. Flanking sequences of SNPs for KASP probes design is deposited in Table 8.

TABLE 6

Differences in the DJ-longevity and virulence between homozygous genotypes of the reference and alternative SNPs of 12 KASP markers along 40 Heterorhabditis bacteriophora wild type strains and inbred lines. The differences between mean $MTS_{50}$ of the homozygous genotypes (days) are depicted as absolute values. Differences in virulence ($LD_{50}$) are depicted as number of DJs. For DJ-longevity, phenotypic data from two treatments (0 and 70 mM $H_2O_2$) under two temperatures (25° C. and 7° C.) were analyzed. For virulence $LD_{50}$ against Tenebrio molitor as used as phenotypic trait. Significance of the differences between genotypes was assessed via ANOVA and Tukey's HSD test ($P \leq 0.05$) and is indicated with stars.

| Marker name | $LD_{50}$ T. molitor $LD_{50}$ difference | $P < 0.05$ | $MTS_{50}$ 25° C. Difference (days) | $P < 0.05$ | $MTS_{50}$ 25° C. 70 mM $H_2O_2$ Difference (days) | $P < 0.05$ | $MTS_{50}$ 7° C. Difference (days) | $P < 0.05$ | $MTS_{50}$ 7° C. 70 mM $H_2O_2$ Difference (days) | $P < 0.05$ |
|---|---|---|---|---|---|---|---|---|---|---|
| EN-Hb_oxid-05173 | | | 0.8 | | 3.7 | * | 5.1 | | 1.6 | |
| EN-Hb_oxid-56985 | | | 0.3 | | 5.2 | * | 8.7 | | 2.2 | |
| SC00003427 | | | 9.2 | * | 3.4 | | 6.2 | | 2.1 | |
| SC00004554 | 1.26 | * | 6.6 | * | 2.4 | | 1.3 | | 1.6 | |
| SC00004647 | | | 7.8 | * | 7.3 | * | 10.7 | * | 4.5 | * |
| SC00004911 | | | 2.6 | | 4.4 | * | 13.6 | | 3.7 | |
| SC00005330 | | | 5.2 | | 8.2 | * | 6.2 | | 2.6 | |
| SC00006203 | | | 7.3 | * | 5.9 | * | 13.2 | * | 4.6 | * |
| SC00010093 | 1.31 | * | 6.0 | * | 0.7 | | 3.3 | | 0.3 | |
| SC00011215 | | | 11.0 | * | 10.2 | * | 8.9 | | 5.2 | * |
| SC00012917 | | | 7.5 | * | 0.3 | | 1.0 | | 0.6 | |
| SC00013602 | | | 0.7 | | 4.5 | * | 9.7 | * | 3.1 | * |

Use of the SNP-Marker Data and Phenotypic Characterization for Selection of a Prominent H. bacteriophora Strain with Better DJ-Longevity and Virulence.

The initial phenotypic information ($MTS_{50}$-70 mM $H_2O_2$, and $LD_{50}$ for T. molitor) was cross checked strain by strain using the genotype information with the objective to choose a WT-natural strain having the following parameters: i) high $MTS_{50}$ value, ii) low $LD_{50}$ value, iii) Strong alleles for the most significant SNPs tested by KASP assays, and iv) high polymorphic level in the tested KASP markers compared to the actual commercial line EN01. Based on this parameters, the WT strain HU2 was chosen for further tests, including performance in the field against the western corn rootworm, persistence, and formulation longevity. Concerning significant KASP markers 8 out of 12 markers (66%) resulted distinctive between HU2 and the commercial EN01 strain and its daughter line IL3. The polymorphic markers

TABLE 7

Genotypes of KASP markers associated to DJ-longevity along the shorter-living commercial H. bacteriophora strain and inbred line (EN01 and IL3, respectively) and the longer living WT strain HU2. For simplicity, the genotypes for the reference and alternative SNPs have been coded with the AB system for each marker individually.

| Marker Name | Longevity Sign. | Virulence Sign. | IL3 | EN01 | HU2 |
|---|---|---|---|---|---|
| SC00003427 | * | | T/T | T/T | G/G |
| SC00004141 | | | A/A | A/A | T/T |
| SC00004554 | * | * | G/G | G/G | A/A |
| SC00004634 | | | C/C | C/C | T/T |
| SC00004647 | * | | C/C | C/C | T/T |
| SC00004911 | * | | C/C | C/C | C/T |
| SC00005330 | * | | G/G | G/G | A/A |
| SC00006203 | * | | C/C | C/C | T/T |
| SC00010093 | * | * | G/G | G/G | A/A |

TABLE 7-continued

Genotypes of KASP markers associated to DJ-longevity along the shorter-living commercial *H. bacteriophora* strain and inbred line (EN01 and IL3, respectively) and the longer living WT strain HU2. For simplicity, the genotypes for the reference and alternative SNPs have been coded with the AB system for each marker individually.

| Marker Name | Longevity Sign. | Virulence Sign. | IL3 | EN01 | HU2 |
|---|---|---|---|---|---|
| SC00011215 | * |  | T/C | T/C | T/C |
| SC00012917 | * |  | C/C | C/C | G/G |
| SC00013602 | * |  | A/A | A/A | A/A |
| EN-Hb_oxid-05173 | * |  | G/G | G/G | G/G |
| EN-Hb_oxid-11688 |  |  | G/G | G/G | C/C |
| EN-Hb_oxid-26008 |  |  | A/A | A/A | G/G |
| EN-Hb_oxid-56985 | * |  | G/G | G/G | G/G |

TABLE 8

Sequences used for KASP assays design for the identification of *H. bacteriophora* SNPs by PCR.

| Marker | Sequence for probe | SEQ ID NO: |
|---|---|---|
| SC00003427 | TTATCAAGTAAATAAAGTTCGTCTATTTTTATTAAGATTTTCTCACTAAAGTGA-TAAGTATG TTG[G/T]AGTTCTTGATTAGTATTAATTAACAGCGATTAAATGCCAGAGAGGCAATAAACG CTGTGTAAACCCACATTAATTTAGCTTTTTCTATTCACAGATTC | 1 |
| SC00004141 | TACATACTTGCATTAAATGGAACAAAGTGCTCATCAATGTGCATTTAGTATTTACATC-TATG TGTATGAAATGTG[T/A]CATCTGTATATTGTGCGAACTTAACAAAGAAAGACTTATTGAGG TCATTTTTATATACATGGTGTCCACGATAAAAGGACCTATTTGACAAGTTTTATAACT | 2 |
| SC00004554 | AATTAAACCGCAGATGACCGAGCCAGGGGTGAGTTTTTCGGTGCACTTCGATGT-GAGTTTGA AGACTGCGAG[G/A]GATGTAAGTTTACTGGTGAGTTTTCCTTTATATTTTTTTTCAGTACT CTCCTGAGCCGAGGCGTTTGCCTCAGTGCTCTTTTCCCACCTCC | 3 |
| SC00004634 | ATCTTTTAGGAAGTACAAAAGATGTATAATTTATTTACTAGTAATAATTCGC-CACGTTCTTC TACTATCCATGTTGATGTTGTCA[T/C]TATGTTTAAGCACTTGATAGGTATATGGATACAC ATCTGAGATTTCGTGTCATTTACTTTACCCCGGTTACTTTTCGGGCTATTTTATACCCTT | 4 |
| SC00004647 | AACTTAGTAATAAAATTCGTAAAAATTATTTTATGCTTACATTCACTCCTATGGACTTC-TAC ATAGAAGGCTTC[C/T]GATGAGCGGGGAATAAGCCCTCGCTGTCCAGTGGCAATATTCATC GCATCCAGTGAACAATCCCTTTAATATGTGAAACTTAAAGTTGG | 5 |
| SC00004911 | GGATCGAGTAAAGTATTAATGACTTCCATGTCGTGGCATTGACCACTTG-GATGTGACAAGAA CCTCAGTGGGAGTCTTTTCTATTCAGCAATAGACTGAAAATAATAATAAA[T/C]AAGAAAT AAACACGTGATATGTGAGAAATAAAGAAACTTATTCAGACAGAT | 12 |
| SC00005330 | CTATTACTACTACTATTACTATTATCAAGTTGAGTTAAATTAATAAAGGTGAAAATAT-TGTG GCATTATTTTTGACATGCCTGTGGTTTGAATCACT[G/A]CTTTTTTTTATCATGATTTTTA TTCTAGAATGGTACCAAAT-TGTATAGTAAAGGCGAAGAACGAAAGGAAGCGAGTATACGTCG GTGAAGAATTATGTGAATGTGCTGATCGAAGCAGCCTATTCTTCGTATTA | 6 |
| SC00006203 | TCACCGAAATATTGTGGTAGAAGTTAGCGTGAGAAGTTGGACTCATATTAGTG[C/T]TATT CATCGAATGGACATGGGAAAACAGTTACTCAGATAACTGTTCCTTTGCCCTGT-GAATAAGGG CAGATTTAATCTTACGGTTACTGGTCTTCATGGCTGAACAACTT | 7 |
| SC00010093 | GTGGCGAGAAGAAAGAATAAGTATTATTTGAAAGATCAATATCCATTAATATGAGT-GAACAA TTGAATAGGACAATAGTTAAATGATAGAAGGTTTAACTCAATGGTTAA[A/G]TTTAAAAAG ATAAGGGAACTACTTCAGACAGGTCTTCGGCGCACGGAATCGGC | 8 |
| SC00011215 | CTTTGCTTATGATACAACTATTAACACTCAGTCTCTTGAAATACATGTGCATGTACAGATG [T/C]TATAAAGACGTATAATACACAATAAATAAAAAATAGAGTAAACATTAGAACAATTTT ATAGATTAGAAAACTATTTACTGAAAAATTTACTGGTATTGATTA | 13 |
| SC00012917 | TTGTTCCATTGTTCAAAAACATTGTAATACTGTCAACTATTGCTTGGAA-CATGTTCTAGAAT AATGGTTCATTGGC[G/C]ATTTGCCGTCATTAGTAATGTTAAAATAGTTTTAATCTGTAGT GGATTTGTGGCGGACGCAGTGGTTGATGCATCAGAATTGTTCCA | 9 |

TABLE 8-continued

Sequences used for KASP assays design for the identification of H. bacteriophora SNPs by PCR.

| Marker | Sequence for probe | SEQ ID NO: |
|---|---|---|
| SC00013602 | GTGTGGTCGTCATTCGATTTGGACACGATTGGGACCCTACATGCATGCGAATGGAT-GAGGTT<br>AGGTTGTTCTCTAACATTTTGGCAAATTTTTTC[G/A]GGACAAACTACATATGCAAATCTT<br>TTATAGACACTGTTCAAAATCGCTCCCAAAATCAAAAATTTCTC | 14 |
| EN-Hb_oxid-05173 | TGGAGTTACCTGCCGCCATTTCATATATTGTCGTTTTAGATGCT-TACTTGTCGCGGACTAAG<br>GGAGAACCTCTTGGAAGACAAGCTCCGGCCCCTGGAAGACTTCCAACTA-CACCAGGCAGGAC<br>TGGCAACCCTTCTATGAAGTTCACTGCAGGAAGCGGCT-CACGAAGCCGAAAATAGCAATCTT<br>TAATGTTTTACCC[G/T]CAATATTGATTAGTATTTTGCTTATGGCCCAATTTCTGAAATGC<br>ATTTTACTATTGTATCATGCAATACAATAATCTTTAATATCGATTTTCAT-CATCAGAGAATG<br>AAATTATTGCAACGAA | 15 |
| EN-Hb_oxid-11688 | GCTTCATGGTTTTAGCCATACAATCGATGATGCCATTATAGGCATT-CATGGTTTGTAGTCTA<br>GCCTTGACTGTGTCCAGCGGATGTCCAACGAGAAGGCCTGCTCCTCCTAACATAT-TAAAGGT<br>CATAGCCGATCTCGCCCGCCCCATTTTCTCAGCGTAAATAATCAATCGAAC-TACGAGAGGTC<br>AACCAAACGGCTG[G/C]ACTGCTTATTGACAGTTTTGCTGTTAGCGTTCTCGTATTTTATA<br>TTTGCACCTCATTATATTTTAGTTTGTCTAATTAAATATATGAACTAATTGA-TAAATAAATA<br>GGTTCTTACTTC | 10 |
| EN-Hb_oxid-26008 | CAAAAATTCCGATCAACATACTTTATACATTTTATCGTTATGAAGTCATTTATTCAT-TGACT<br>GAGAAAAATATAAGTGAAGAGCCACTAATTAATCGATATATAAGTAGCTACAAGATT-GATTT<br>TTAATACTATTGTAAATAATAATTAGTTAAATGCATTGTAGCAAATTAAAA[G/A]CTAATG<br>ATCTAAGAAAATCCCGGAAGAAAAGGATACGAAACGGTCATCTAACAACGC-TATAATAATTA<br>TGCAGTTTTAATTTTCTTGCTATTAAAAAATCGTAACAATAACATTGATA-CATATATATCGA<br>TTAATTAGTGGCTCTTCACTTATATTTTTCTCAGTCAATGAATAAATGACTTCATAAC-GATA<br>AAATGT | 11 |
| EN-Hb_oxid-56985 | GTGTGGTAGTTTTATGTCACGAGCTGGAAGTAGACAGTCTTTCACAAGTTGATCCT-TAACAA<br>GTGTTTCATTGAAATGCCATAAACCTATAAAAAGACTTATGAAT-TTTTTCTGCTAACTAGGT<br>CTCCGGTTTCGAATCCAATGAGAACGCGATAATAGGCTCTAATGGAAACCCAAA-GATCTTTC<br>ACTTGATCAGCCAC[G/A]GCATCAACTAAGGCTTCTTCGAAAGGCGTCTTTCCAGCAAAAC<br>CAAACTTTCTGGCTAAATATCTTGCACCTGCATAGGATTGACCAATCTGTTTCCCAT-CAACC<br>TCAAGGATAGGGACCTGTCCAAATGGCATTGTTGCTTTATACTTTGGCCACATGTCAAT-TGG<br>TATGCGGTAATCTTCATACTCCTGGCCTGCTAG | 16 |

Testing the Performance of HU2 and HU2-IL1 and the HUPT Cross Progeny

After having chosen the HU2 strain as a candidate strain for nematodes breeding, an inbred lined derived from this strain (HU2-IL1) was additionally crossed with the highly virulent but low-surviving inbred line (PT1-IL), derived from the PT1 strain. The pooled progeny of this cross (hereafter HUPT) was also subsequently tested for its performance on the lab and on the field, together with the HU2 strain and the actual commercial line EN01.

Methods

Virulence Screening in H. bacteriophora WT Strains and Inbred Lines Against Mealworm Mealworms (Tenebrio molitor) were used as hosts for the virulence characterization of H. bacteriophora WT materials. Nematode suspension volumes of 1.0 ml (Ringer's solution) from each strain and line containing 80, 200, 400, 800 and 2000 DJs ml-1 were inoculated in the middle of the Petri dishes and incubated at 25° C. for 7 days. Four replicates were done for each nematode quantity and strain. Infection by DJs was checked with the luminometer LUMAT LB 9501 (Berthold GmbH, Germany). The mean mortality by nematode infection of T. molitor was compared among 42 strains (40 strains+1 mutant strain+1 strain pool). Mortality data was used to calculate the lethal dose of DJs required to kill 50% of the insect larvae per assay ($LD_{50}$).

Virulence Screening in H. bacteriophora WT Strains and Inbred Lines Against the Western Corn Rootworm (Diabrotica virgifera)

Parallel to T. molitor assays, sand biotests containing 20 D. virgifera virgifera larvae were set as described above calibrating the sand moisture to 10%. Larvae of Diabrotica virgifera virgifera were provided by BTL Bio-Test Labor GmbH Sagerheide (Groß Lüsewitz, Germany). As a food source for WCR each Petri dish was supplied with a one-week old maize seedling (cultivar Ronaldinio). Nematode suspension volumes of 1.0 ml (Ringer's solution) from each tested strain and line containing 100, 200, 400, 800, 1600, and 3200 DJs ml-1 were inoculated. After seven days, the mortality of the larvae was confirmed as described above. Mortality data was used to calculate the lethal dose of DJs required to kill 50% of the insect larvae per assay ($LD_{50}$).

DJ-Persistence Characterization in Cross-Progenies and Selected Materials

To evaluate the performance of materials selected along WP2. Persistence assays were carried out as described above. Each Petri dish was supplied with a one-week old maize seedling. Persistence was assessed using the following *H. bacteriophora* strains: PT1-IL1, HU2-IL1, HUPT and sel-HUPT. Nematode concentrations of 400, 800, 1,600, 3,200 and 6,400 DJs in 1 ml of Ringer's solution were inoculated in the middle of the plate and incubated at 25° C. inside a humidity box (with water at the base preventing the plates to dry out). After 3, 4 and 5 weeks of storage, twenty larvae (third instar) of *D. virgifera virgifera* were supplied along with a new maize seedling and stored at 25° C. After seven days, the mortality of insect larvae was observed and nematode infectivity was confirmed by checking luminescence using Luminometer. The $LD_{50}$ for each replicate was calculated.

Nematode Survival Estimation in Cross-Progenies and Selected Materials

The persistence of *H. bacteriophora* DJs is influenced by the virulence and the survival over time from the tested strain. We determined the DJ-survival on the bioassays over time in our promissory materials. For this, petri dishes (150 mm) were filled with sand (150 g with 10% moisture) and provided with a one week old maize seedling per plate. Nematodes at amounts of 400 and 6400 DJs per petri dish were inoculated in several petri dishes per tested material. Petri dishes were stored at 15° C. and 25° C. The DJs were extracted from the entire 150 g sand out of each bioassay Petri dish using a stirring and decantation process (Cobb 1918). Subsequently DJs in aliquots of the decanted solutions were counted. This procedure was repeated over extended storage times. Dauer juveniles extracted on day 1 were taken as the starting population. The percentage of DJs that survived after 1, 2, 3 and 5 weeks of incubation was calculated. To check whether the reduction of infection rate after nematode incubation is due to DJs mortality and/or declined virulence, $LD_{50}$ was recalculated based on the survival data over time.

Assessment of Persistence of *H. bacteriophora* Strains Under Semi-Field Conditions In order to assess the persistence of the studied strains under intermediary conditions between lab and field, trials with maize plants were carried out in wood containers under uncontrolled environmental conditions in the outdoor area of the applicant. Two independent trials were launched. Within each trial, wood containers had space for four pots of 29×29×25 cm. Each pot received a tiny layer of stones and was fully filled with soil. The initial soil moisture was adjusted to 45% water content. Soil moisture and temperature were monitored by a mini-logger (PlantCare Ltd., Russikon, Switzerland). Three nematode materials were selected for the first semi-field trials: the commercial strain EN01, the high-longevity and virulent strain HU2, and the selected cross progeny sel-HUPT. The strains were tested at two application dosages (1×109 and 2×109 DJs ha-1). The first trial started in April 2017 whereas the second trial was started by the end of May 2017. In the second trial, the non-selected cross progeny HUPT, and the parental inbred line with high virulence and longevity HU2-IL1 were also included. Five replicates were done per strain in each trial. Pots were randomly distributed over nine and fourteen containers in the first and second experiment, respectively. Nematode persistence was assessed up to 71 days after inoculation of nematodes by non-destructive baiting as previously described. Seven days after each baiting event, tubes were removed from the soil and the insect mortality was recorded. Dead insects were individually checked for luminescence of the symbiotic bacteria under a luminometer.

Field Trials for the Control of the Western Corn Rootworm

For field trials, the high-virulent and high-longevity *H. bacteriophora* HU2 strain was chosen, along with the commercial strain EN01. Dauer juveniles of both strains were produced in large volume fermenters (500 and 3.000 litres) and were harvested and formulated according to the ENE SOP.

Nematode Efficacy in Naturally Infested Field Plots (Styria, Austria) in 2016 and 2017

Field trials were carried out to evaluate the efficacy of the HU2 and EN01 strain in Austrian locations (Styria) along the maize growing seasons of 2016 and 2017. Nematodes were applied in two with western corn rootworm naturally infested maize field at the sites Unterschwarza and Lichendorf. In 2016, nematode treatments consisted on DJ applications of strains HU2 and EN01 at the commercial dose (2×109 DJs ha-1). Additionally, a combination of EN01 with Rhizovital was evaluated aside untreated controls and parcels treated with the chemical insecticide Belem. In the field trials of 2017 treatments consisted of the two above mentioned *H. bacteriophora* strains at two application dosages (1×109 and 2×109 DJs ha-1) aside untreated controls and parcels treated with the chemical insecticide Belem. For both seasons, study parcels consisted of 30 rows of 30 m length for nematode treatments and 12 rows for untreated control. The number of emerged beetles in all parcels was determined by the use of photoeclectors. The plants damage level registered at plant maturity. Plants were rated according to the degree of stem inclination into: upright plants, plants with inclined stems, and plants with "gooseneck" stem. Soil baiting from the different parcels was done using the Falcon tube method described above. Baiting was done 9 weeks after nematode application. Each Falcon tube received 18 g of soil, ten *T. molitor* larvae, and one maize seedling. Tubes were buried at 10 cm deep in the soil and left in soil contact for 10 days. Baiting was done at five replicates per treatment. At the end of the baiting period, tubes were recollected and shipped to ENE, where the infection of *T. molitor* larvae with EPNs was recorded.

Nematode Efficacy in Artificially Infested Field Plots (CABI, Hungary) in 2016 and 2017

Field trials were conducted as well in Hungary in 2016 and 2017. The trials were carried out in each maize growing season in two conventionally managed maize fields, referred to as field Q and R for 2016, and referred to as S and T for 2017 trials. The field site is located southeast of Kondoros village in the Bekes County in Southern Hungary. Both fields had no natural population of western corn rootworm due to crop rotation, i.e. Triticale, had been planted the previous season, thus interrupting the pest life cycle. All fields had been ploughed in autumn of the previous cropping season and they were tilled and harrowed on April of both trial years. Sowing was carried out on the 18th and 25th of April 2016 and 2017, respectively. In 2016, treatments consisted of DJs of strains HU2 and EN01 at the commercial dose (2×109 DJs ha-1), aside parcels treated with the insecticide Cypermethrin and untreated controls. In 2017 Treatments consisted on the two *H. bacteriophora* strains mentioned above at the doses of 1×109 and 2×109 DJs ha-1. In each field, 4 parcels of 6 rows (4.5×20 m each) were used per treatment and 5 parcels for the controls. Following, *D. v. virgifera* eggs were infested in treated and untreated plots (control). Among the 4 middle rows, 2×6 successive maize plants (≈1.2 meters) were randomly chosen of each of the 6-row wide plots and were infested with 500 ready-to-hatch *D. virgifera* eggs per plant. Eggs were applied into two 100 to 140 mm-deep holes at a distance of 110 to 190 mm from both sides of the plant, deep into the soil towards the maize roots. Assessment of nematode persistence was done using the Falcon tube baiting method, ten replicates per treatment and control. All together 10 tubes×5 treatments×2 fields=100 tubes were put into the field. Assessment of treatment efficacy in reducing *D. v. virgifera* was done by cutting 6 consecutive plants for all treatments and covering them with gauze cages (Toepfer et al. 2008) at the predicted beetle emergence time. Adult emergence within the cages was recorded weekly following the procedures outlined in the EPPO standards for this pest. Root damage was assessed in dog-out plants using the EPPO scale (Anonymous, 1999) and the traditional Iowa scale (Hills and Peters, 1971). Field trials in Hungary were performed by CABI (Stefan Toepfer).

Results on Nematode Performance

Virulence Comparison Between the *H. bacteriophora* Commercial Line and the Lines Derived in the Course of BIOCOMES WP2.

Figure 7:
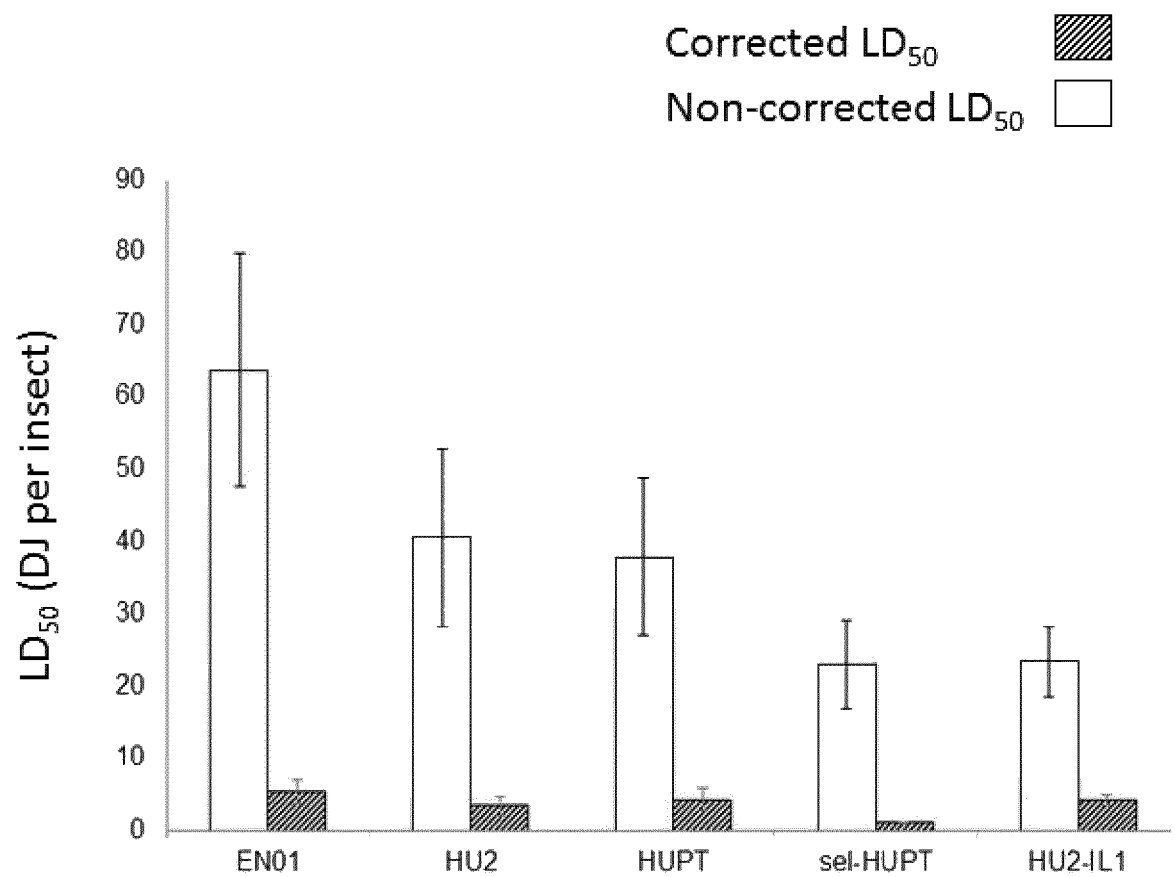
FIG. 7 shows the mean $LD_{50}$ against *D. v. virgifera* of the *Heterorhabditis bacteriophora* commercial strain EN01 along materials characterized within BIOCOMES WP2 (HU2, HUPT, sel-HUPT and HU2-IL1. Persistence was assessed after six weeks of incubation at 17° C. in sand bio-assays and seven days of incubation at 25° C. $LD_{50}$ was corrected (black bars) according to DJs survival after mechanic extraction. Error bars: SEM of two replicates. No significant differences were determined between strains (Tukey's HSD test at P≤0.05).

The virulence of the materials developed along the BIOCOMES WP2 was tested in comparison to the current commercial line. For this characterization, DJs from the EN01, HU2, HU2-IL1, HUPT and sel-HUPT were grown in parallel under sterile liquid culture conditions. After standard sand bioassays all the tested *H. bacteriophora* materials were able to infect *T. molitor* and *D. v. virgifera*. On *T. molitor*, significant differences were observed among the $LD_{50}$ (F=5.09; df=4, 44; P≤0.002). Against this host, $LD_{50}$ values ranged from 1.7 to 36.5 DJs per mealworm larva (FIG. 7). The virulence of sel-HUPT ($LD_{50}$=6.5±1.1) and HU2-IL1 ($LD_{50}$=5.1±0.37) was significantly lower than the commercial strain EN01. An intermediate virulence was recorded for HU2 ($LD_{50}$=10.54±1.17) and the HUPT pool ($LD_{50}$=8.13±0.78). No significant difference between strain infectivity was observed against *D. v. virgifera* (F=2.295; df=4, 17; P≤0.101). However, the lowest $LD_{50}$ was observed for HU2-IL1 (8.25±1.71 DJs per insect) and HUPT (10.8±0.86 DJs per insect).

Persistence Evaluation in Sand Bioassays

Figure 8:
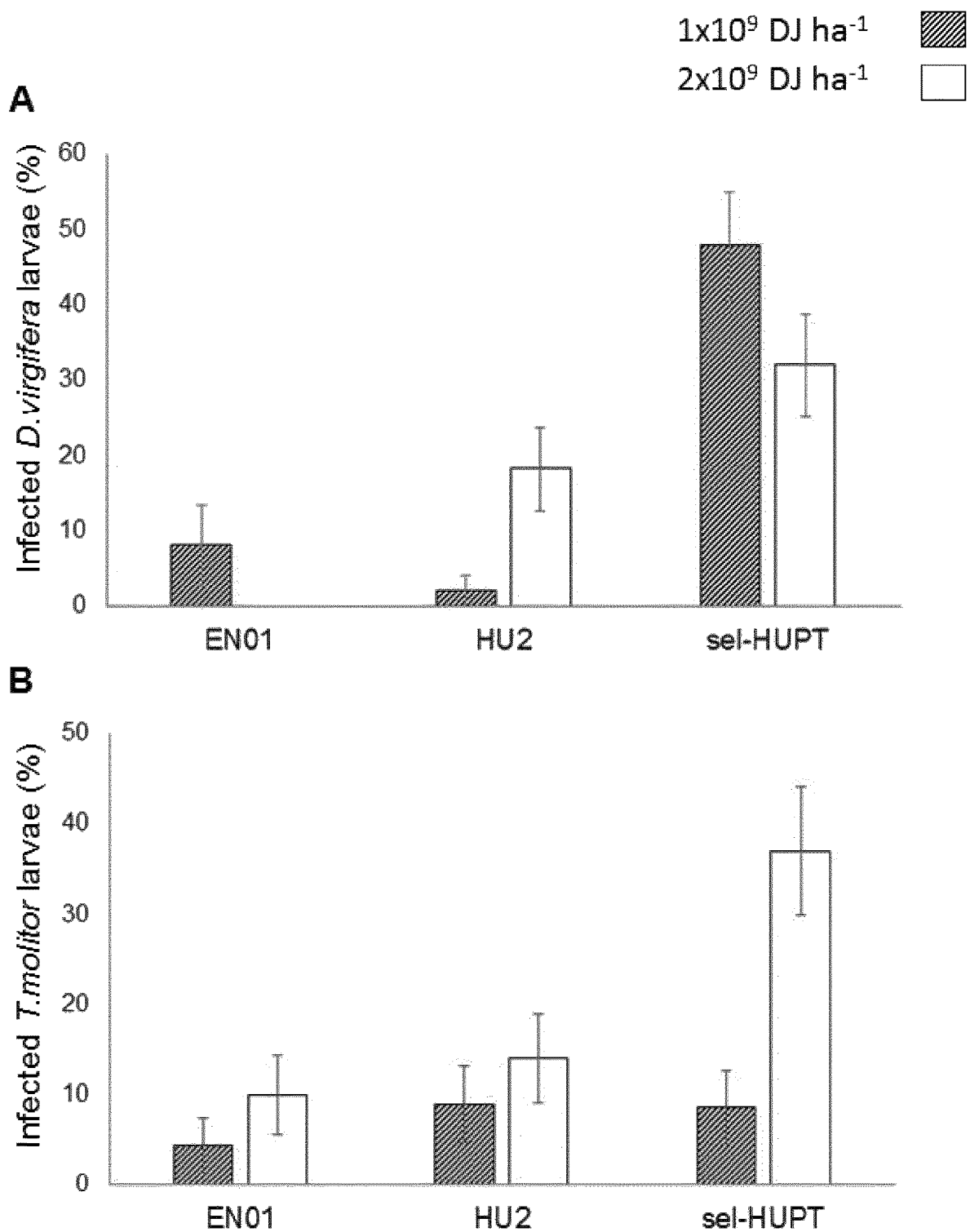
FIG. 8 shows the infected hosts (%) after 21 days of DJ application calculated for the *Heterorhabditis bacteriophora* commercial strain EN01 and two strains characterized along BIOCOMES WP2 (HU2 and sel-HUPT). Doses of 1×109 (reduced dose) and 2×109 DJs ha-1 (commercial dose) were evaluated against *Diabrotica v. virgifera* (A) and *Tenebrio molitor* (B). Stars above the bars indicate significant differences between doses, for each strain and host. Letters above the bars indicate differences between strains for each dosage (Tukey's HSD test at P≤0.05).

The $LD_{50}$ of our selected *H. bacteriophora* strains was assessed after six weeks of DJs inoculation in sand plates at 17° C., followed by one week of incubation at 25° C. in presence of twenty *Diabrotica virgifera* larvae. Subsequent to the assay, the number of living DJs on the plates was determined, and was used as correction factor for the $LD_{50}$ (corrected-$LD_{50}$). An overview of the non-corrected $LD_{50}$ (based on inoculated DJs) and the corrected $LD_{50}$ against western corn rootworm larvae is depicted in FIG. 8. After six weeks, all the tested *H. bacteriophora* strains presented corrected-$LD_{50}$ values lower than 10 DJs per insect. Uncorrected-$LD_{50}$ ranged between 63.7±16.2 and 22.9±4 DJs per insect. The higher number of living DJs extracted from the soil was found for HU2-IL1 whereas the lowest was found for sel-HUPT (data not-shown). The highest virulence after the incubation time was determined for the HU2 and sel-HUPT materials, with $LD_{50}$ values of 1±0.2 and 3.35±1.8 DJs per insect, respectively. Both corrected and uncorrected data followed similar pattern for $LD_{50}$, wherein the strains EN01 and sel-HUPT presented the highest $LD_{50}$ (lowest virulence) and lowest $LD_{50}$ (highest virulence), respectively. Due to experimental variability, the difference between strains was statistically not significant (F=1.122; df=4; P≤0.222 and F=2.076; df=4; P≤0.440 for uncorrected and corrected data, respectively).

Persistence Evaluation in Soil Pot Bioassays

Figure 9:
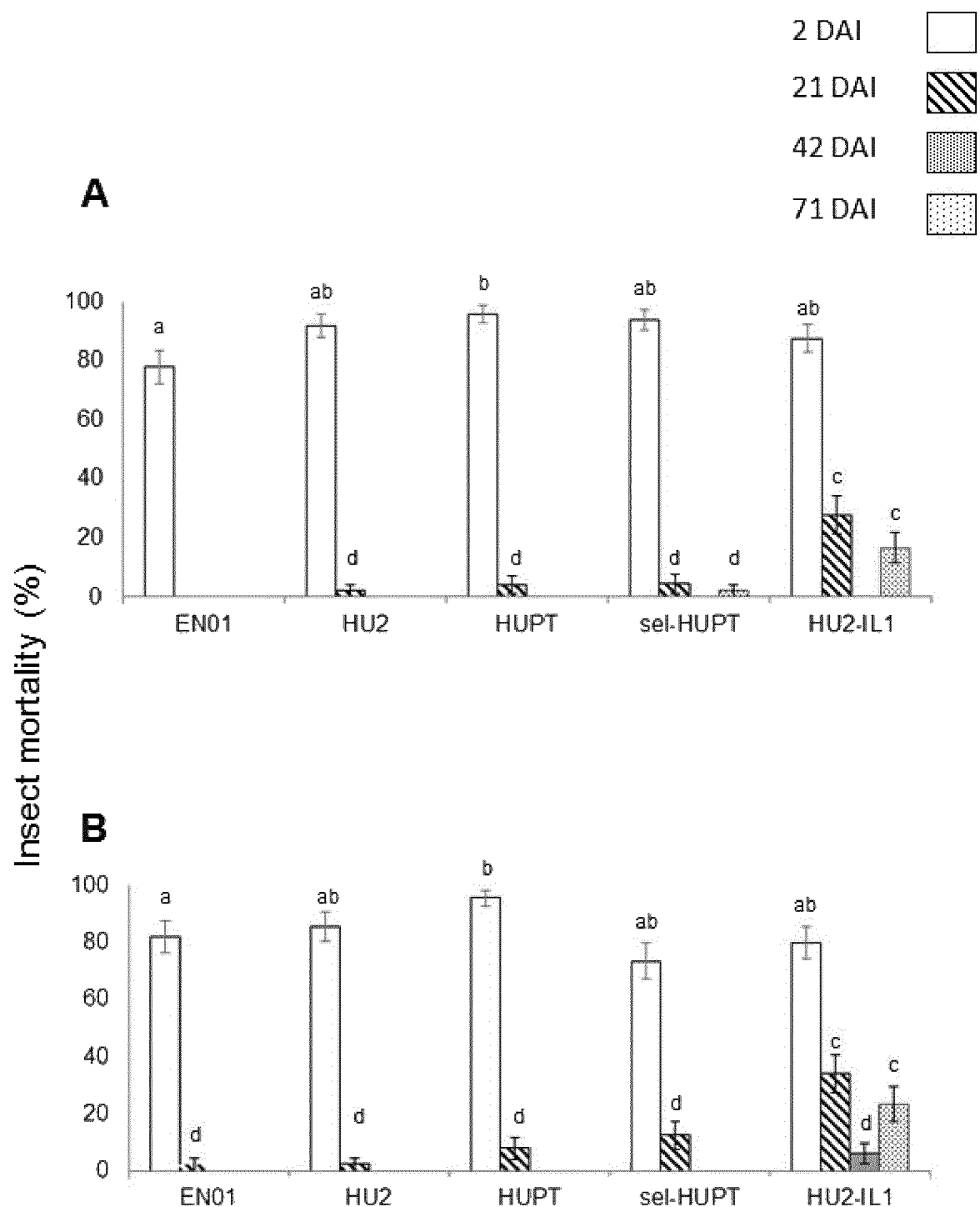
FIG. 9 shows the infected *Tenebrio molitor* larvae percentage over time in a semi-field experiment. DJs of the *Heterorhabditis bacteriophora* commercial strain (EN01) and strains and inbred lines characterized along BIOCOMES WP2 (HU2, HUPT, sel-HUPT and HU2-IL1) were applied. Two application doses were tested: 1×109 DJs ha-1 (A) and the commercial dose of 2×109 DJs ha-1 (B). Baiting was done using the Falcon tube method with ten insects per tube. Error bars: SD of five replicates. Different letters on the error bars indicate significant differences between groups (P≤0.05). No significant differences between dosages of the same strain were determined.

Parallel to sand bioassays, evaluation of the persistence in soil pots of two strains characterized along BIOCOMES WP2 (HU2, sel-HUPT) was compared with the current commercial strain EN01 (FIG. 9). The experiment was conducted in the ENE laboratory at room temperature conditions (25±2° C.). Nematodes were applied at doses representing the commercial application (2×109 DJs ha-1) and half of the required DJs (1×109 DJs ha-1). Nematode persistence was assessed according to the number of infected bait insects (*T. molitor* or *D. v. virgifera*) over 63 days after nematodes application. After 21 days of DJ application, to most drastic differences between strains and doses were observed. For D. v. *virgifera*, the highest infection percentage was observed for sel-HUPT (47.8±7.1) with half of the commercial dose, whereas the lowest infection percentage was observed for the commercial strain EN01 with the commercial dose (no infection registered). For *T. molitor*, the highest infection percentage was determined for sel-HUPT with the commercial dose (37.0±7.1), whereas the lowest infection percentage was determined for the commercial strain with half of the commercial dose (4.4±3.0). Forty-two days after DJs application, only few insects were found infected. No significant differences were determined when comparing both doses against the same host, with exception of sel-HUPT against *T. molitor* (F=7.9; df=1; P≤0.022). A positive correlation between *T. molitor* and *D. v. virgifera* larval mortality due to overtime nematode infection was observed ($R^2$=0.8435; P≤0.0001).

Persistence Evaluation in Semi-Field Conditions

Figure 10:
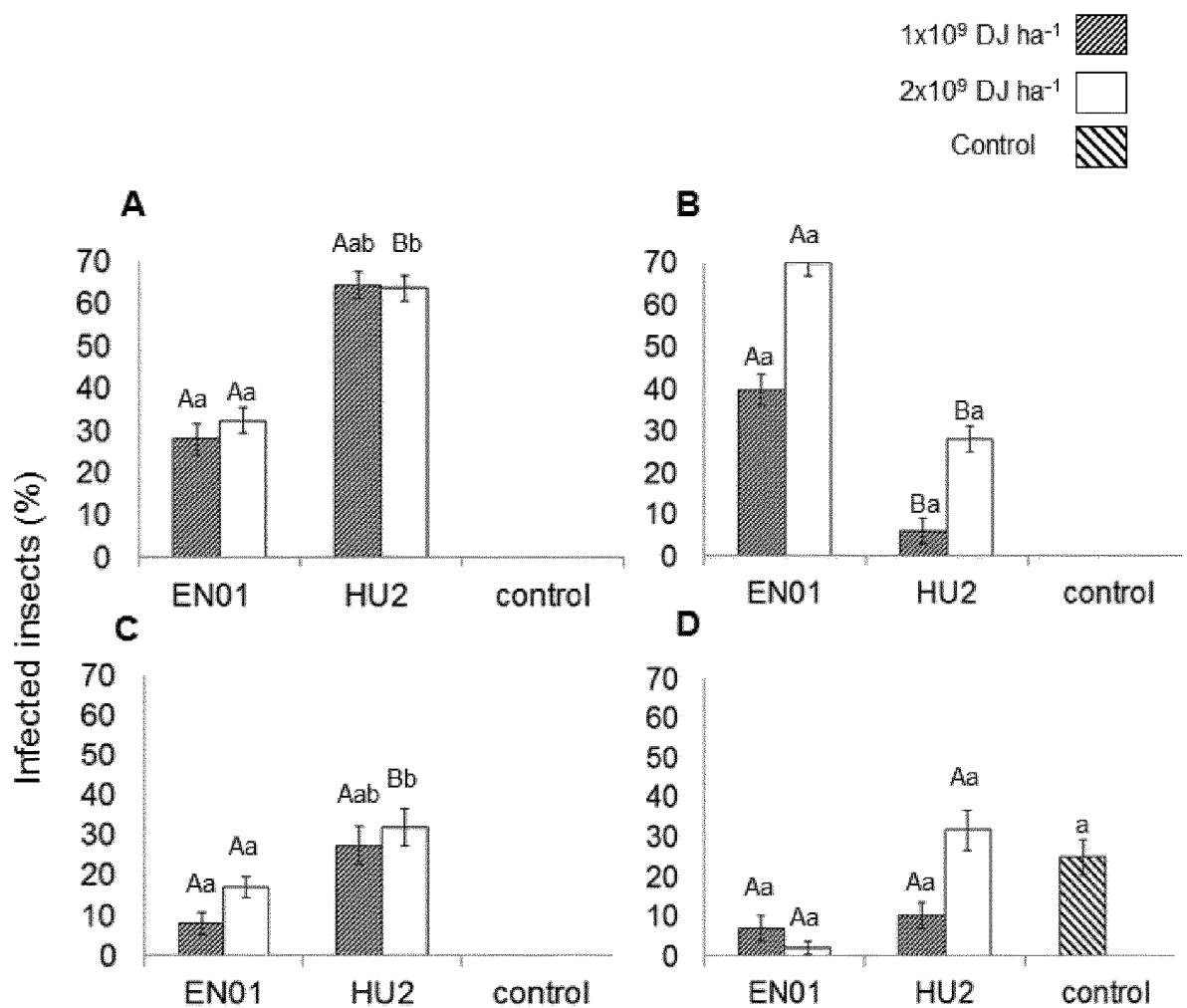
FIG. 10 shows the insect mortality after baiting experiments in field trials in 2017. Field trials in Styria (Austria) were carried out in Unterschwarza (A) and Lichendorf (B). For Austrian sites, baiting was done two 60 days post-DJs-application using the Falcon tube method containing 10 *Tenebrio molitor* larvae per tube and 5 replicates per treatment. Field trials in Hungary were carried out in two fields of the Kondoros site: Field-S and Field-T (C and D, respectively). For Hungarian sites, baiting was done two 80 days post-DJs-application using the Falcon tube method containing 10 *T. molitor* larvae per tube and 5 replicates per treatment. Different letters on the error bars represent significant differences within fields. Two application DJ doses were evaluated: commercial DJ dose (2×109 DJs ha-1, white bars), and a reduced dose (1×109 DJs ha-1, black bars).

Semi-field experiments were carried out at ENE under free environment conditions for the persistence evaluation. Two experiments were carried out in April and May respectively. The experiment started in April was exposed to unfavourable cold temperatures after sowing, not representing the real application scenario whereas the May trial went under favourable conditions (hereafter analysed in detail). For the current experiments, the baiting method based on falcon tubes was used as described under materials and methods. For this experiments, only *T. molitor* larvae were used for baiting. Along the May trial, bait mortality declined along time (cf. FIG. 10). Twenty-one days after DJs application in the semi-field pots, the insect mortality dropped abruptly down to an overall infectivity lower than 10%. At this time a significant difference in bait mortality for the strain HU2-IL1 was determined in relation to the commercial strain EN01 (P≤0.036) and HU2 (P≤0.047). In general, mortality due to nematode infection ranged from 28±6.4 to 34±6.7 percent of infected insects. Further on, 42 days after DJs application, insect mortality was only determined by baiting pots inoculated with HU2-IL1 applied at 2×109 DJs ha-1 (FIG. 10). At the last baiting time (71 days after DJs application), only positive baiting was detected in pots inoculated with sel-HUPT and HU2-IL1 DJs. Pots infected with half of the commercial dose of sel-HUPT DJs presented one sample containing infected insects (2±2% of insect mortality), whereas no infectivity was recorded with the commercial dose. In pots inoculated with HU2-IL1 DJs, insect mortality due to nematode infection ranged from 16.6±5.3 to 23.3±6 percent; here most of the samples (60-80%) presented at least one infected insect (Table 3).

Persistence Evaluation from Baiting in Field-Trials in 2017

Figure 11:
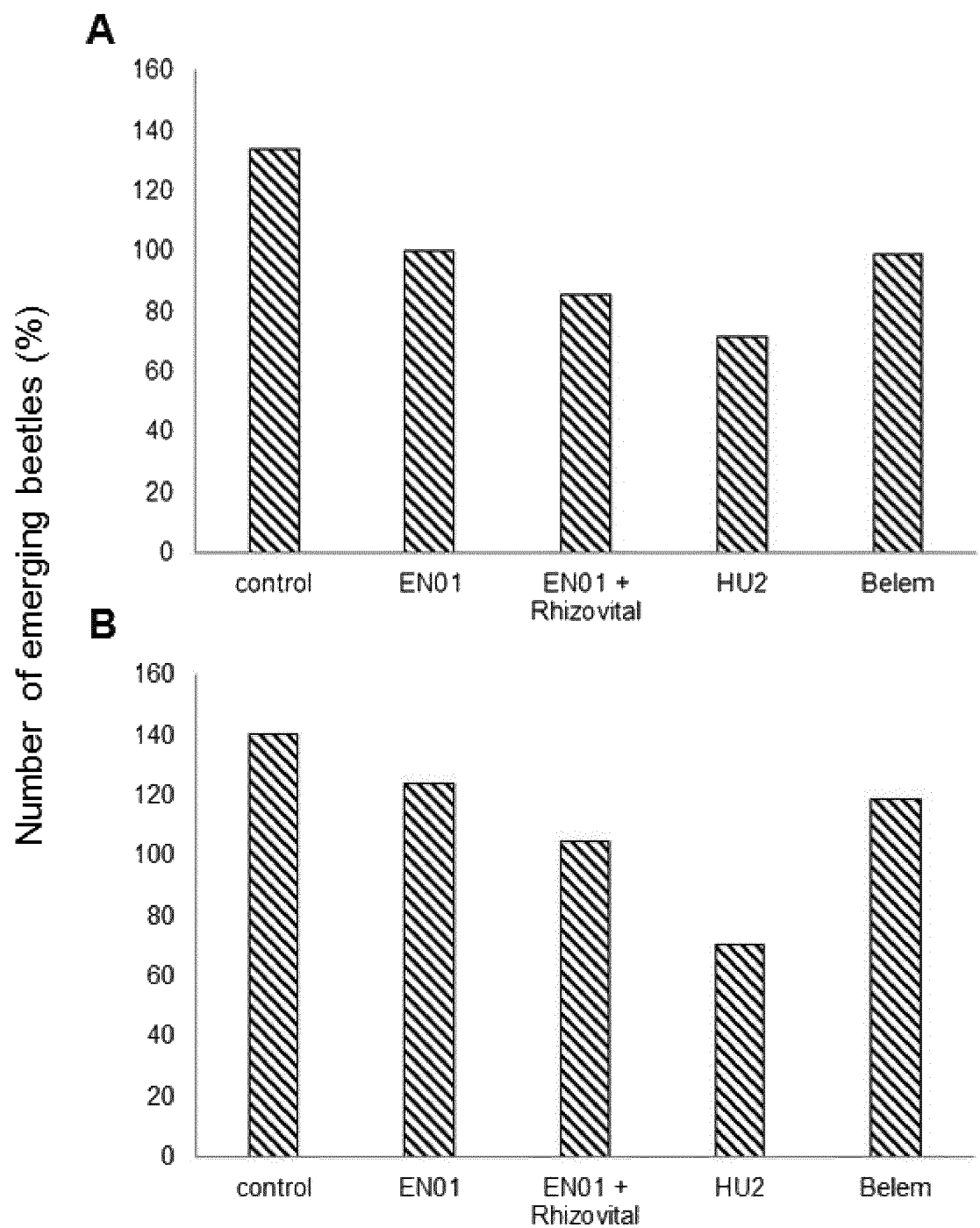
FIG. 11 shows the number of emerging *D. v. virgifera* in Austrian field sites Unterschwarza (A) and Lichendorf (B) in field trials in 2016. Control untreated maize parcels were compared against chemically treated-(Belem) and DJ-treated parcels. Two *Heterorhabditis bacteriophora* strains were evaluated (EN01 and HU2), at 2×109 DJs ha-1. Additionally, the combination of commercial DJs and Rhizovital was assessed. Emerging beetles were registered by photoeclectors.

In the final stage of BIOCOMES WP2, evaluation of promissory materials in field trials was carried out. For this purpose, the strain HU2 was chosen in first instance. The overall performance of this strain was higher than the current commercial strain EN01. In 2016 and 2017 both strains were produced in parallel in large fermenters and were applied in Austrian and Hungarian sites. Concerning 2017, the strains were applied in maize field trials in Austria (field sites Unterschwarza and Lichendorf) and in Hungary (field sites Kondoros S and Kondoros T). In 2017 both strains were applied at the commercial dose (2×109 DJs ha-1) and the reduced dose (1×109 DJs ha-1). Concerning the Austrian sites in Styria, on the Unterschwarza fields, no significant differences were observed on application dosage (K=3.652; df=3; P≤0.302). In general, insect mortality due to nematode infection in the field was higher for the strain HU2, ranging from 64±6.9 and 64±7 percent, whereas for the commercial strain EN01 insect mortality ranged from 28±7.1 to 33±6.7 percent (FIG. 11). In this site, control parcels (no DJ application) yielded not infected hosts. In the Lichendorf site, the current commercial strain yielded higher infection rates after baiting. Insect mortality by nematode infection ranged between 40±6.9 to 70±6.5 percent (EN01) and 6±3.3 to 28±6.3 percent (HU2). Differences between strains were significant (F=7.969; df=11.449; P≤0.012). Concerning the application dose, no significant differences were determined (EN01: F=2.161; df=1, 8; P≤0.180; HU2: F=2.839; df=1, 8; P≤0.130).

In Hungary in 2017, two fields were analysed in the Kondoros site (field T and Field S). In the Kondoros field S, significant differences in insect mortality were found between parcels where DJs were applied in comparison to control parcels (K=14.82; df=3; P≤0.002). In this site, the HU2 strain presented higher infection rate after baiting (31.78±4.65 to 31.78±5.2 percent of infected insects) compared to EN01 (8±2.78 to 17±3.79 percent of infected insects), as shown in FIG. 11. This infection rate was significant from DJs of the strain HU2. Considering the application dose, significant differences were only observed for strain EN01 (K=5.78; df=1; P≤0.016). Considering the applied dose, a higher number of infected tubes were observed for the highest application dosage in the field Kondoros S, whereas no differences were determined for Kondoros field T. Despite the high variability associated to field trials, the HU2 strain showed in general (3 out of 4 fields) a better performance that EN01 using the commercial dose (2×109 DJs ha-1), whereas in 2 out 4 fields the performance was better than EN01 using half of the commercially applied DJs (FIG. 11)

Trials in Fields Naturally Infested with WCR (Styria, Austria, 2016 and 2017)

Main Results from Field Trials on 2016

Figure 12:
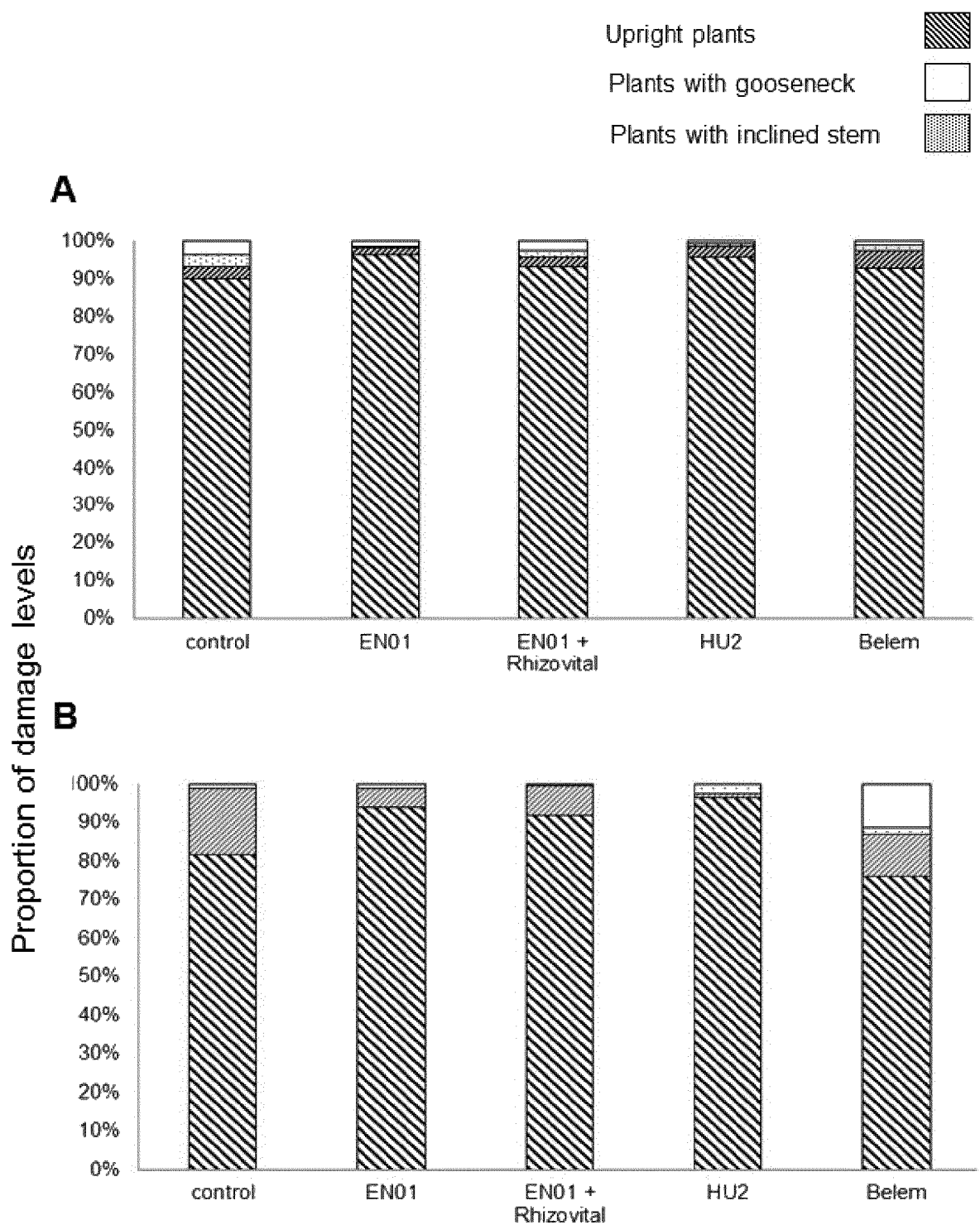
FIG. 12 shows the plant damage levels (%) per plant treatment in the Austrian field sites Unterschwarza (A) and Lichendorf (B) in field trials in 2016. Control untreated maize parcels were compared against chemically treated-(Belem) and DJ-treated parcels. Two *Heterorhabditis bacteriophora* strains were evaluated (EN01 and HU2), at 2×109 DJs ha-1. Additionally, the combination of commercial DJs and Rhizovital was assessed. Plants were evaluated according to the strength of their stem in the categories depicted above.
Figure 13:
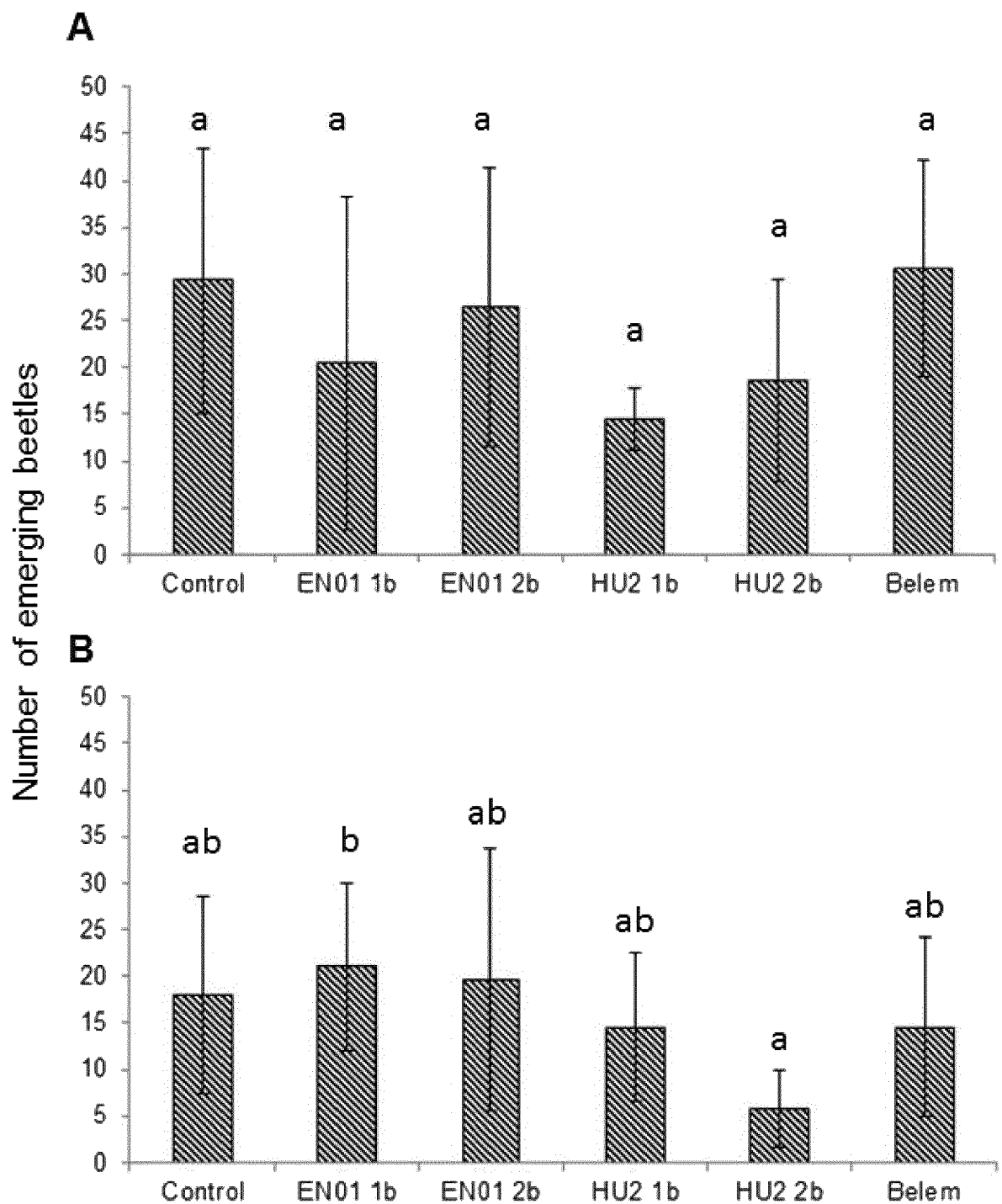
FIG. 13 shows the number of emerging *D. v. virgifera* in Austrian field sites Unterschwarza (A) and Lichendorf (B) in field trials in 2017. Control untreated maize parcels were compared against chemically treated-(Belem) and DJ-treated parcels. Two *Heterorhabditis bacteriophora* strains were evaluated (EN01 and HU2), at two doses each: 1×109 DJs ha-1 (1b) and 2×109 DJs ha-1 (2b). Emerging beetles were registered by photoeclectors. Significant letters denote significant differences among treatments within one field for Unterschwarza (Tukey's HSD test at P≤0.05) and Lichendorf (Conover-Iman test with Bonferroni correction at P≤0.05). Error bars: SD.

Field trials were carried out in two field sites in Austria: Unterschwarza and Lichenhof. For both strains, the commercial dose was used (2×109 DJs ha-1). Parcels treated with the chemical insecticide Belem, and untreated controls were evaluated. Additionally, a mixed treatment (EN01 DJs+Rhizovital) was evaluated. Concerning the registered number of emerging *D. v. virgifera* beetles, parcels treated with DJs of the HU2 strain showed less number of beetles in both evaluated field sites compared to the chemical control. Concerning the commercial line performance, the results show a same level with Belem. As may be expected, untreated controls showed the highest number of registered emerging *D. v. virgifera* beetles (FIG. 12). Concerning the aspect of the plants on the treated parcels, no major differences on the treatments were observed on the Unterschwarza field site, whereas in the Lichendorf field site, the proportion of upright plants was higher in the parcel treated with HU2 DJs (96.3%). In this field the lowest proportion of healthy plants was shown in the parcel treated with Belem (76.1%) followed by the control parcel (81.7%) as shown in FIG. 13. In general the performance of the DJ treatment was equal or better than the chemical control. The lower number of emerged beetles in contrast to EN01 and the higher proportion of upright plants determined for parcels treated with HU2 strain indicate a general better performance of this material.

Main Results from Field Trials on 2017

Figure 14:
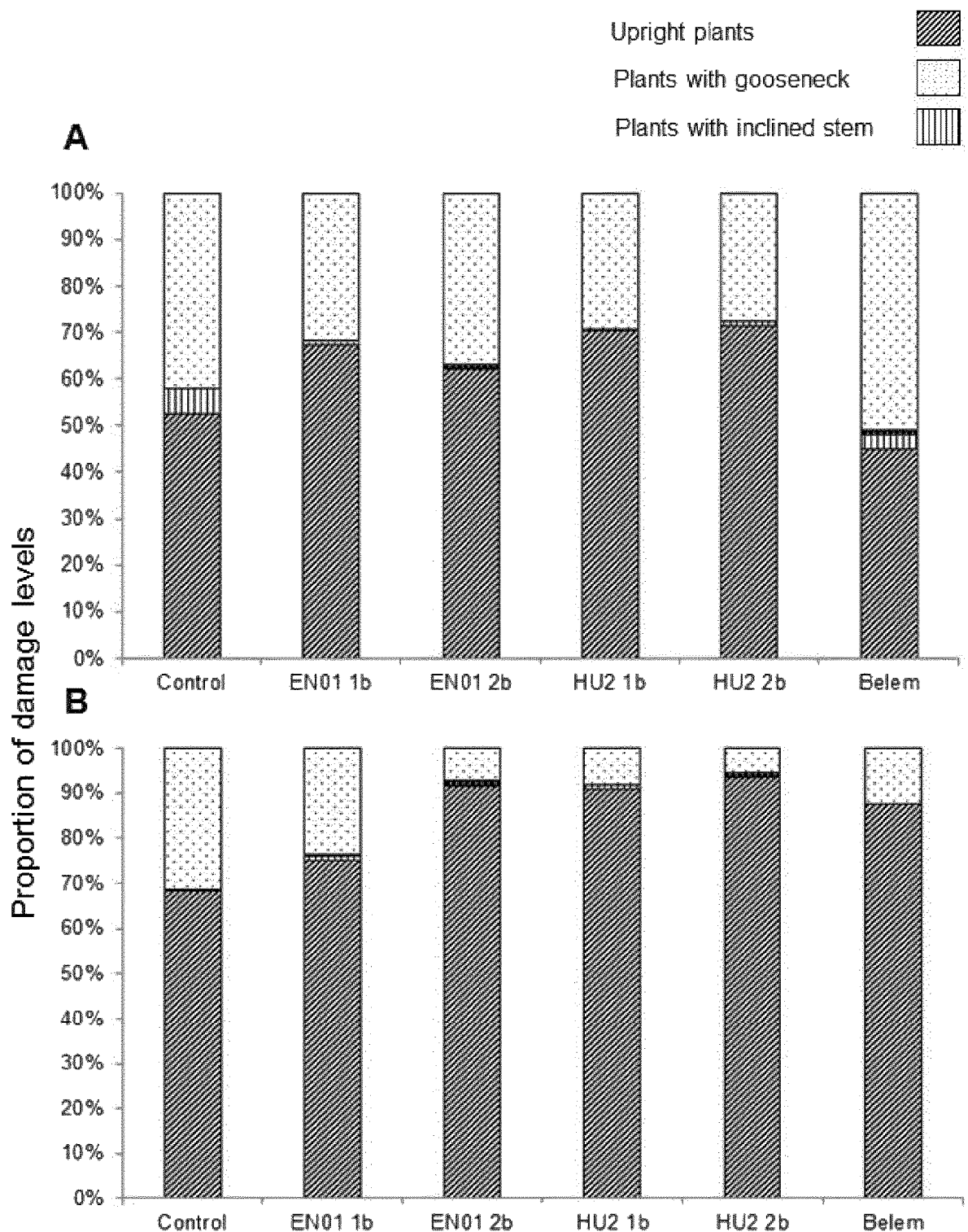
FIG. 14 shows the plant damage levels (%) per plant treatment in the Austrian field sites Unterschwarza (A) and Lichendorf (B) in field trials in 2017. Control untreated maize parcels were compared against chemically treated—(Belem) and DJ-treated parcels. Two *Heterorhabditis bacteriophora* strains were evaluated (EN01 and HU2), at two doses each: 1×109 DJs ha-1 (1b) and 2×109 DJs ha-1 (2b). Plants were evaluated according to the strength of their stem in the categories depicted above.
Figures 15, 16:
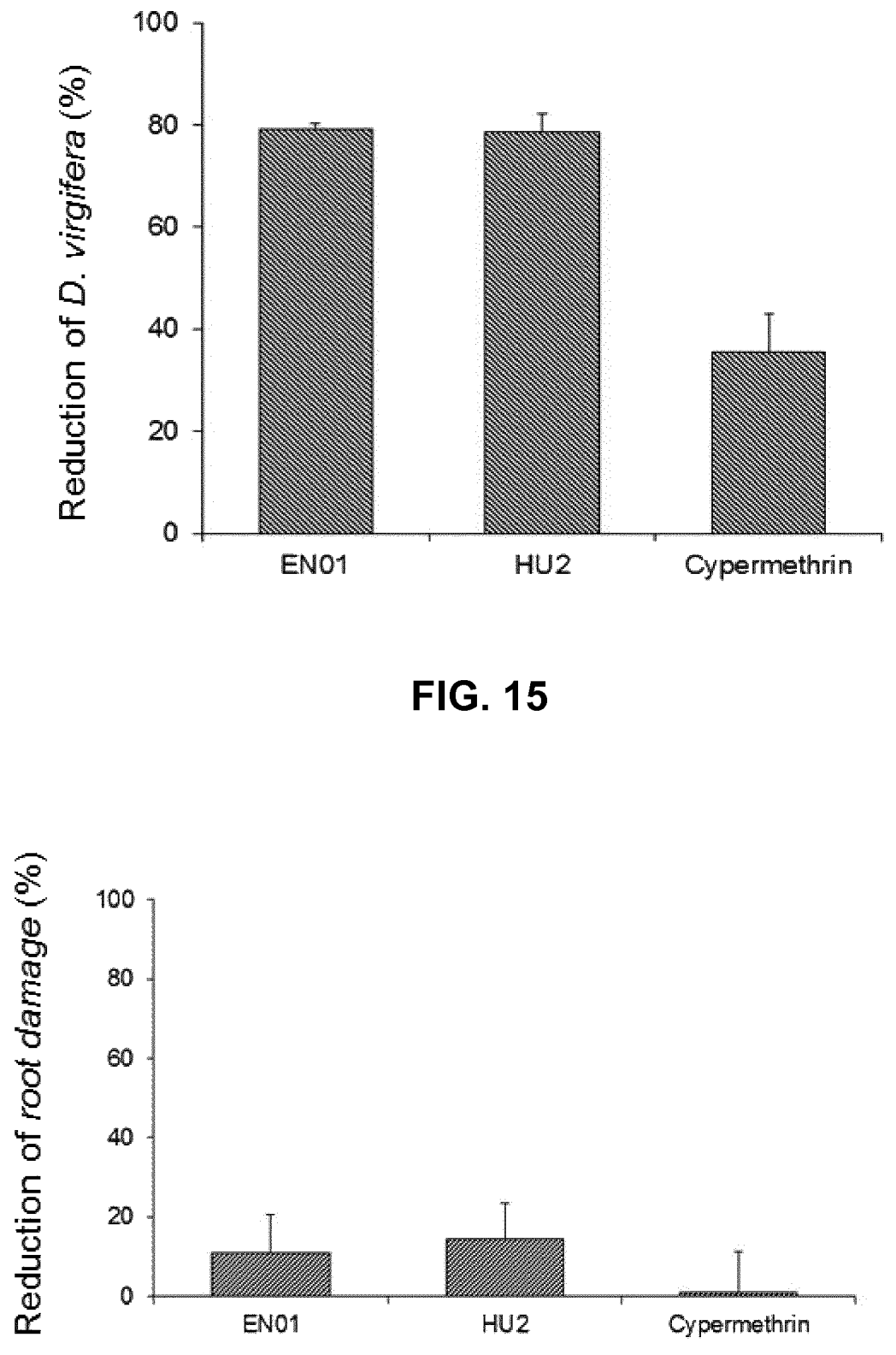

The field trials in the Austrian locations in 2017 were evaluated for pest parameters as well as plant appearance. Concerning pest parameters, the number of emerging beetles was surveyed in the Unterschwarza and Lichendorf sites. In Unterschwarza, no significant differences were observed in the number of emerged *D. v. virgifera* beetles, neither for the treatment, nor for the strain or the DJ dose (FIG. 14). However, parcels treated with HU2 DJs either at 1×109 DJs ha-1 or 1×109 DJs ha-1 showed the lowest numbers of emerging beetles (FIG. 14). In the Lichendorf site, results showed an improved performance on HU2 compared to the other DJ treatments, to the chemically treated parcels, and the non-treated parcels (FIG. 14). Regarding appearance of the plants, parcels with DJ treatment showed either comparable results or better performance than parcels treated with chemical insecticide Belem. In both sites, Unterschwarza and Lichendorf, HU2-treated field showed plants with the least damage (FIG. 15). In parcels were HU2 DJs were applied, at least 70% of the evaluated maize plants where in upright position, whereas the percentage of healthy plants was lower in untreated fields. Interestingly, in both field sites both of the HU2 doses were better than the chemical treatment (cf. FIG. 15).

Trials in Fields Artificially Infested with *Diabrotica virgifera virgifera* (Hungary, 2016 and 2017)

Main Results from Field Trials on 2016

Figure 17:
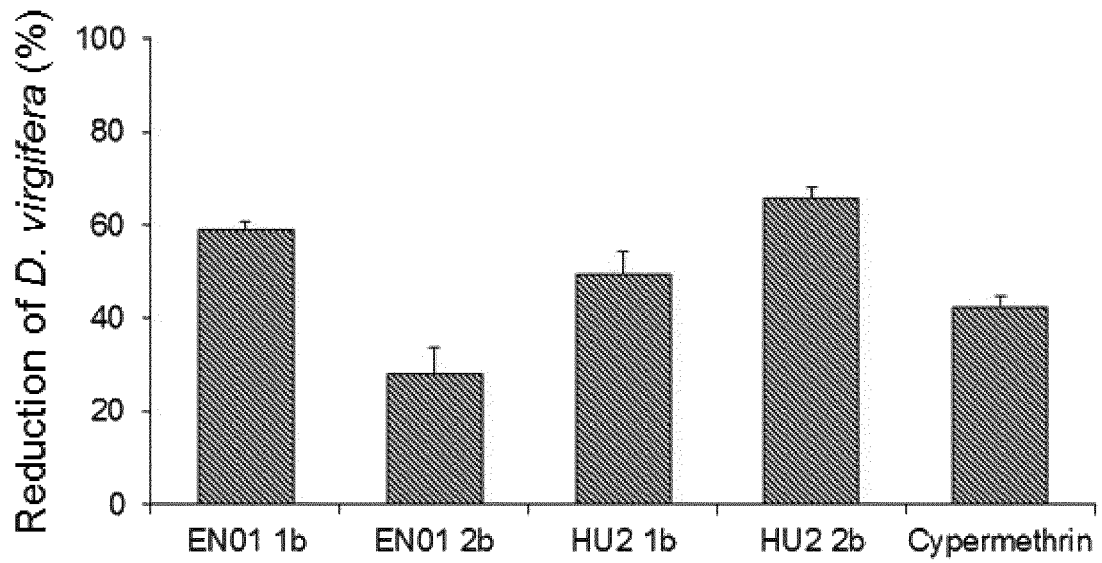
FIG. 17 shows the efficacy (%) of nematodes and chemical insecticide (Cypermethrin, 12 kg ha-1) treatments in reduction of *Diabrotica v. virgifera* in artificially-infested field trials in Hungarian sites in 2017. All treatments are compared against the untreated control parcels. Emerging adults were counted upon application of 100 eggs per plant. Nematodes from the EN01 and HU2 strains were applied at a reduced dose of 1×109 DJs ha-1 (1b) and the commercial dose of 2×109 DJs ha-1 (2b). Error bars: SD from two fields.

Results from field trials in the Hungarian sites in 2017 revealed that both nematode strains largely and comparably reduced *D. v. virgifera* populations after survey of adults emerged per 100 applied *D. v. virgifera* eggs per plant. The efficacy of EN01 ranged from 74 to 84% (Mean 79.1%), whereas HU2 showed an efficacy of 60 to 97% (Mean 78.7%). Interestingly, in the parcels controlled with the chemical insecticide Cypermethrin the efficacy of the treatment against *D. v. virgifera* was only of 35.4% (FIG. 16). Concerning the plants degree of damage, for parcels where nematodes were applied only 7 to 16% prevention in root damage was achieved according to the Iowa Scale (FIG. 17). Also in this case, the level of prevention determined in parcels treated with Cypermethrin was even lower.

Main Results from Field Trials on 2017

Figure 18:
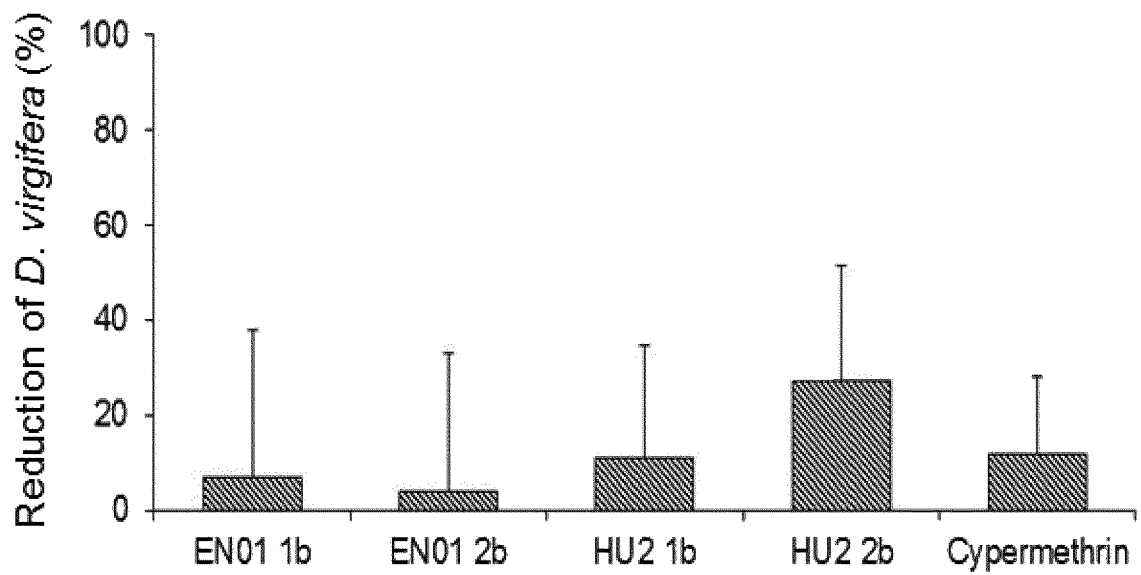
FIG. 18 shows the efficacy (%) of DJ and chemical insecticide (Cypermethrin 12 kg ha-1) treatments in reduction the plant root damage (IWOA scale) in artificially-infested field trials in Hungarian sites in 2017. All treatments are compared against the untreated control parcels. Nematodes from the EN01 and HU2 strains were applied at a reduced dose of 1×109 DJs ha-1 (1b) and the commercial dose of 2×109 DJs ha-1 (2b). Error bars: SD from two fields.
Figure 19:
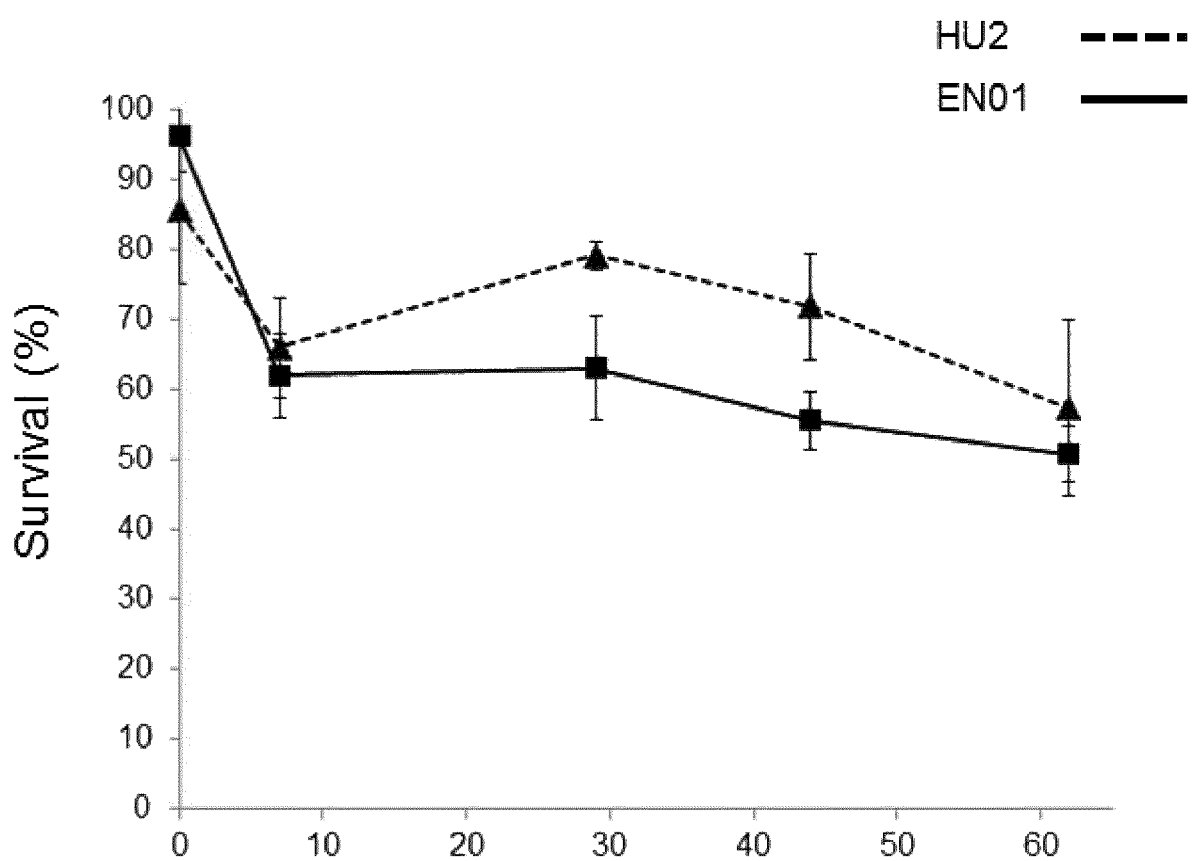
FIG. 19 depicts the percentage survival of two *Heterorhabdits bacteriophora* strains EN01 (blue line) and HU2 (red line) stored at 6° C. in formulation. Storage time: days after formulation. Error bars: SD of three sub-samples per strain and time point. Different letters show significant differences within the same time point (Tukey's test; P≤0.05).

Similarly to the field trials in 2017 carried out in the Austrian locations, field trials in Hungary in this year were carried with the nematode strains EN01 and HU2 at the commercial dose (2×109 DJs ha-1) an the reduced dose (1×109 DJs ha-1). Concerning adult emergence after artificial egg infestation, both nematode strains reduced *D. v. virgifera* populations at both application dosses (EN01=28 to 57%, HU2=49 to 66% efficacy) compared to the untreated parcel. However, discrepancies were observed among fields (FIG. 18). No measurable results were observed for EN01 at 2×109 DJs ha-1 in one parcel of field S, whereas the same phenomenon was observed for HU2 at 1×109 DJs ha-1 in one parcel of field T. Thus no major conclusions could be withdrawn by comparing both strains at both DJ-doses. As observed in the previous year, the insecticide Cypermethrin showed only 42±2% control efficacy against *D. v. virgifera*. Overall, only the only parcels with HU2 applied at 2×109 DJs ha-1 showed significant reduction of plant damage (27%). However, this reduction was higher than the level achieved by Cypermethrin (12% damage prevention), as shown in FIG. 19. Despite the variability on the observed results, general better performance of the HU2 strain compared to the chemical insecticide and to the current commercial strain can be suggested. This result is supported by the data from parallel field trials carried out in the Austrian sites shown in the previous sections.

Evaluating the Storage Potential of New Strains Against the Commercial EN01 Strain Apart from field trials, the storage potential after powder formulation was evaluated in HU2 and related strains in comparison to the commercial strain. For this, both strains were industrially produced in 500 and 3000 L fermenters. Normally, DJs are stored only for very short time in powder before they are delivered. With this row of experiments, the possibility of prolonged storage was assessed.

Methods

Powder Formulation of DJs

For DJs grown in liquid cultures or fermenters, washed DJs from HU2 and EN01 were formulated at 1×106 DJ g-1. The formulated nematodes were packed in 5 g zip locked plastic bags. Pinholes were made for each bag to provide aeration inside the bags. HU2 and EN01 were packed in 25 g samples in plastic bags.

Survival of Formulated DJs

To determine the percentage survival along time of DJs produced in bioreactors, formulated nematodes were re-suspended periodically after the formulation date by dissolving the complete sample from one bag in 1 L tap water per gram of formulated powder. Thereafter, 20 µl aliquots from the dissolved DJs were counted under the microscope using a counting chamber. Measurements were done for each sample in triplicate. Total active and not-active nematodes were registered for each aliquot. The percentage of survival was calculated using the formula: the total living IJs g-1*100 divide by number of nematodes at the start of the experiment.

DJ-Longevity on Formulated DJs

Oxidative stress assays were performed with nematodes (HU2 and EN01) extracted from the formulation Infective juveniles were transferred to 24-cell wells in 400 µl final volume containing ~3,000 IJs per cell well and kept at 25° C. For each tested strain, four $H_2O_2$ dosages were applied in three technical replicates (0, 40, 80, and 100 mM $H_2O_2$ final concentration). Dosages and strains were arranged in a randomized manner. Infective juvenile survival was recorded for a period of 12 days after stress induction by counting living and dead individuals in a counting chamber (20 µl aliquots from each assay). The IJs mortality was used to determine the mean tolerated $H_2O_2$ dose (LC50–$H_2O_2$) for each line.

Virulence in Post-Formulated DJs

DJs suspensions were cleaned from the formulation powder by cotton trapping. Thereafter, the IJs density was counted as described above. Bioassays were carried out in 15 cm diameter Petri dishes filled with sand as previously described for $LD_{50}$ calculation. Control plates received 1 ml Ringer's solution.

Results on Performance of Long-Term Formulated DJs

Post-Formulation Survival in the HU2 and EN01 Strain

Figure 20:
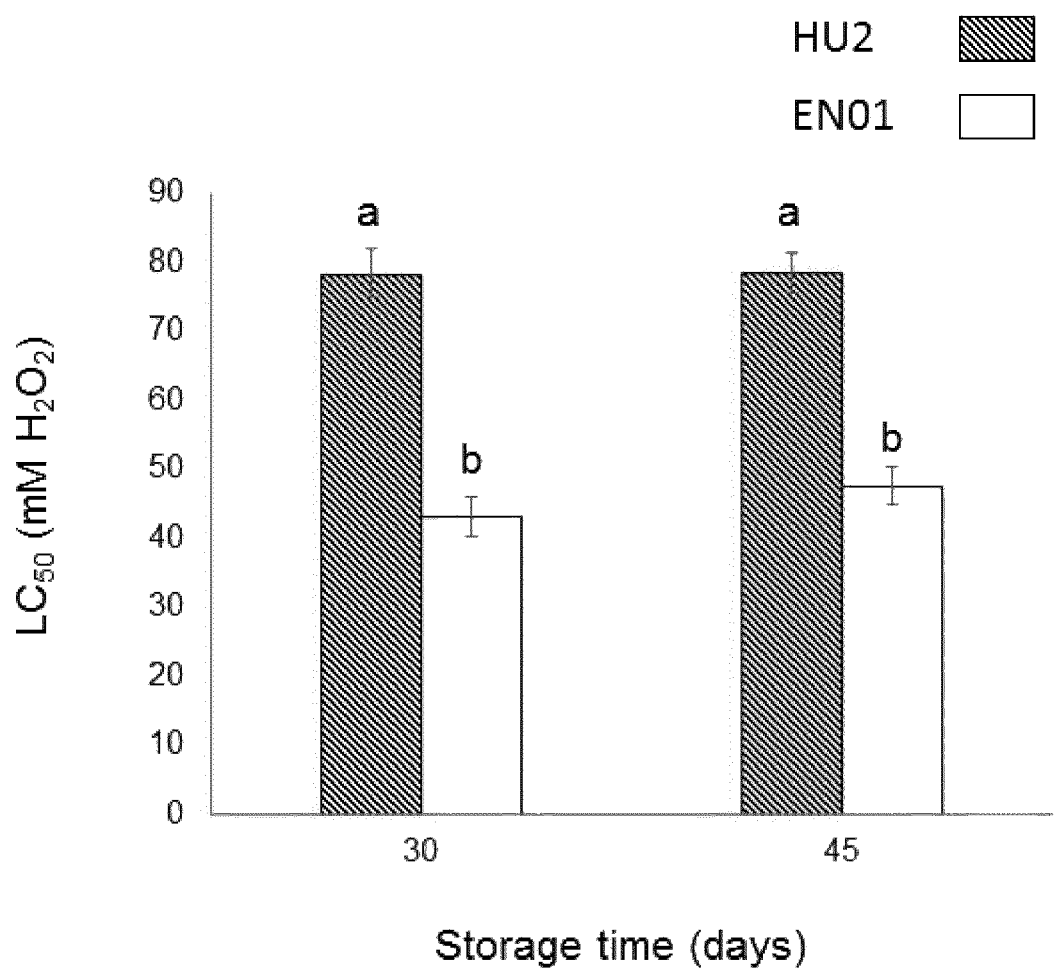
FIG. 20 shows the mean tolerated $H_2O_2$ concentration (in mM) at which 50% of the nematode population survived on day 12 ($LC_{50}$ $H_2O_2$) of strains HU2 and ENO1 stored at 6° C. in powder formulation for 30 or 45 days. Error bars: Standard deviation from three replicates. Different letters on the bars denote significant differences within one time point (Tukey's Test, P≤0.05).

The post-formulation survival of HU2 and EN01 after cold storage (6° C.) was monitored for a period of two months (60 days). The percentage of surviving nematodes over storage time is documented in (FIG. 20). For both strains the mayor decrease in the percentage survival was observed one week after formulation. For the HU2 strain a decrease in survival was observed from 96% down to 62% in these first 7 days. For EN01, the survival decreased from 85% down to 66% in the same time period. Between the 2nd and the 8th weeks, the survival for both strains decreased at lower rate. At the day 62, the HU2 and EN01 strains presented survival percentages of 51 and 57, respectively. No significant differences in the survival were determined between the strains after test at the latest time point.

Post-Formulation Oxidative Stress Tolerance Strains HU2 and EN01

Figure 21:
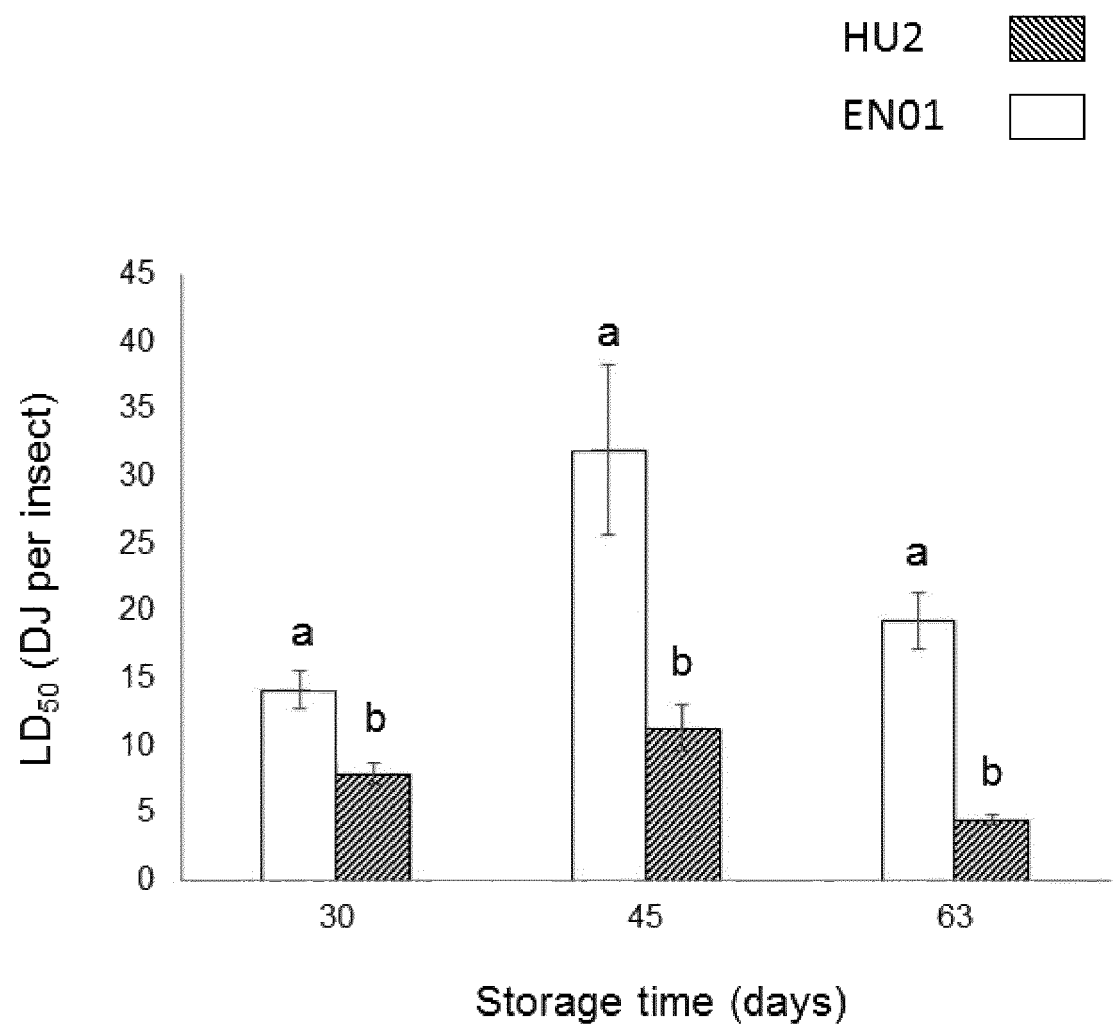
FIG. 21 shows the mean lethal doses ($LD_{50}$) of IJs extracted from formulation of strains HU2 and EN01 over storage period of up to 62 days at 60 C. Error bars: Standard deviation of three replicates. Different letters on bars denote significant differences within each time point (Tukey's test, P≤0.05).

As a second parameter to estimate the performance of the HU2 strain in comparison to EN01, the oxidative stress bioassay was carried out along the cold-storage time of 30 and 45 days with IJs extracted from the formulation. The mean $H_2O_2$ concentrations (LC50) lethal for 50% of the population after 12 days treatment was assessed (FIG. 21). After 30 days of cold storage in formulation, $LC_{50}$ values of 79±4 mM and 43±3 mM $H_2O_2$ were determined for HU2 and EN01, respectively. This large difference in LC50 values between both strains was conserved also after 45 days of storage. At this time point, the LC50 values of 78±3 and 47±3 were determined for HU2 and EN01, respectively. The differences in $H_2O_2$-tolerance between both strains were significant ($F=217.7$, $df=1$, $P<0.05$). These results suggest that DJs from the HU2 strain conserve a better longevity potential than EN01 after cold storage.

Virulence of Post-Formulated DJs of HU2 and EN01

The mean lethal dose per insect for IJs of both strains was determined after 30, 45, and 62 days of storage (FIG. 21). After 30 days of storage, a $LD_{50}$ of 14 and 8 DJs per insect were determined for EN01 and HU2, respectively. After 45 days, the $LD_{50}$ increased for both strains (the virulence decreased) but not in the same dimension. At this time point, the EN01 $LD_{50}$ increased to ~32 IJs per insect, whereas the $LD_{50}$ for HU2 slightly increased to 11 IJs per insect. The tendency concerning the large $LD_{50}$ differences between lines relative to each other was conserved after 62 days of storage. However, both $LD_{50}$ values decreased in relation to the previous measurement. At this observation time point, $LD_{50}$ values of 5 and 19 IJs per insect were determined for HU2 and EN01, respectively. After statistical analysis, significant differences in virulence between HU2 and EN01 strains were confirmed for storage after 30 days ($DF=1$, $P\leq0.05$, $HSD=3.927$), after 45 days (ANOVA, $DF=1$, $F=19,612$, $P<0.011$, $HSD=3.927$) and after 62 days (ANOVA, $DF=1$, $F=100.3$, $\alpha\leq0.008$, $HSD=3.927$).

LITERATURE

Bai X., Adams B J, Ciche T A, Clifton S, Gaugler R, Hogenhout S A, Spieth J, Sternberg P W, Wilson R K, Grewal P S (2009) Transcriptomic analysis of the entomopathogenic nematode *Heterorhabditis bacteriophora* TTO1. BMC genomics 10:205.

Cobb N A (1918) Estimating the population of the soil, with special reference to the sugar-beet and root-gall nemas, Heterodera schachtii Schmidt and Heterodera radicicola (Greef) Muller, and with a description of *Tylencholaimus aequalis* n. sp. USDA, Agricultural Technical Circle 1:1-47.

Ehlers R-U (2001) Mass production of entomopathogenic nematodes for plant protection. Applied Microbiology and Biotechnology 56:623-633.

Ehlers R.-U, Oestergaard J, Hollmer S, Wingen M, Strauch O. (2005). Genetic selection for heat tolerance and low temperature activity of the entomopathogenic nematode-bacterium-complex *Heterorhabditis bacteriophora-Photorhabdus luminescens*. Biocontrol 50, 699-716.

Elshire R J, Glaubitz J C, Sun Q, Poland J A, Kawamoto K, Buckler E S, Mitchell S E (2011) A robust, simple genotyping-by-sequencing (GBS) approach for high diversity species. PloS one 6: e19379.

Grewal P S, Wang X, Taylor R A J (2002). Dauer juvenile longevity and stress tolerance in natural populations of entomopathogenic nematodes: is there a relationship? International Journal for Parasitology 32, 717-725.

Grewal P S, Ehlers R-U, Shapiro-Ilan D I (Eds) (2005a). Nematodes as biocontrol agents. Wallingford, UK, CAB International.

Grewal P S, Peters A (2005). Formulation and quality control of entomopathogenic nematodes. In: Grewal, P. S., Ehlers, R.-U. & Shapiro-Ilan, D. (Eds). Nematodes as biocontrol agents. Wallingford, UK, CAB International, pp. 79-90.

Hills T M, Peters D C (1971) A method of evaluating post planting insecticide treatments for control of western corn rootworm larvae. Journal of Economic Entomology 64:764-765.

Iraki N, Salah N, Sansour M A, Segal D, Glazer I, Johnigk S A, Hussein M A, Ehlers R-U (2000) Isolation and characterization of two entomopathogenic nematode strains, *Heterorhabditis indica* (*Nematoda, Rhabditida*), from the West Bank, Palestinian Territories. Journal of Applied Entomology 124:375-380.

Kiss J, Komaromi J, Bayar K, Edwards C R, Hatala-Hsellér I (2005) Western Corn Rootworm (*Diabrotica virgifera virgifera* LeConte) and the crop rotation system in Europe. In: Vidal S, Kuhlmann U, Edwards C R (Eds) Western Corn Rootworm: Ecology and Management. Wellingford, UK. CAB International pp. 189-220.

Krysan J L, Smith R F (1987) Systematics of the *virgifera* species group of *Diabrotica* (*Coleoptera*: Chrysomelidae: Galerucinae). Entomography 5:375-484.

Long S J, Richardson P N, Fenlon J S (2000) Influence of temperature on the infectivity of entomopathogenic nematodes (Steinernema and *Heterorhabditis* spp.) to larvae and pupae of the vine weevil *Otiorhynchus sulcatus* (*Coleoptera*: Curculionidae). Nematology 2:309-17.

Mukuka J, Strauch O, Ehlers R-U (2010) Variability in desiccation tolerance among different strains of the entomopathogenic nematode *Heterorhabditis bacteriophora*. Communications in Agricultural and Applied Biological Sciences 73:669-72.

Mukuka J, Strauch O, Nellas Sumaya N H, Ehlers R-U (2010b) Improvement of heat and desiccation tolerance in *Heterorhabditis bacteriophora* through cross-breeding of tolerant strains and successive genetic selection. BioControl 55:511-521.

Poinar G O (1975) Description and Biology of a new Insect parasitic Rhabditoid, *Heterorhabditis bacteriophora* N. Gen., N. Sp. (Rhabditida; Heterorhabditidae N. Fam.). Nematologica 21:463-470.

Regeai S, Dolan K, Fitzpatrick D A, Browne J, Jones J, Burnell A (2009) Novel primers for the amplification of nuclear DNA introns in the entomopathogenic nematode *Heterorhabditis bacteriophora* and their cross-amplification in seven other *Heterorhabditis* species. Molecular ecology resources 9:421-424.

Shapiro-Ilan D I, Hazir S, Lete L (2015) Viability and virulence of entomopathogenic nematodes exposed to ultraviolet radiation. Journal of Nematology 47:184-189.

Strauch O, Oestergaard J, Hollmer S, Ehlers R-U (2004) Genetic improvement of the desiccation tolerance of the entomopathogenic nematode *Heterorhabditis bacteriophora* through selective breeding. Biological Control 31:218-226.

Sumaya N H, Aryal S, Vandenbossche B, Barg M, Doerfler V, Strauch O, Molina C, Ehlers R-U (2017) Phenotyping dauer juvenile oxidative stress tolerance, longevity and persistence within wild type and inbred lines of the entomopathogenic nematode *Heterorhabditis bacteriophora*. Nematology.

Sumaya N H, Gohil R, Okolo C, Addis T, Doerfler A, Molina C, Ehlers R-U (2017b) Applying inbreeding, hybridization and mutagenesis to improve oxidative stress tolerance and longevity of the entomopathogenic nematode *Heterorhabditis bacteriophora*. Journal of Invertebrate Pathology (in revision).

Toepfer S, Gueldenzoph C, Ehlers R U, Kuhlmann U (2005) Screening of entomopathogenic nematodes for virulence against the invasive western corn rootworm, *Diabrotica virgifera virgifera* (*Coleoptera*: Chrysomelidae) in Europe. Bulletin of entomological research 95:473-82.

Toepfer S, Peters A, Ehlers R-U, Kuhlmann U (2008) Comparative assessment of the efficacy of entomopathogenic nematode species at reducing Western Corn Rootworm larvae and root damage in maize. Journal of Applied Entomology 132:337-348.

Toepfer S, Burger R, Ehlers R-U, Peters A, Kuhlmann U (2010) Controlling western corn rootworm larvae with entomopathogenic nematodes: Effect of application techniques on plant-scale efficacy. Journal of Applied Entomology 134:467-480.

Vadnal J, Ratnappan R, Keaney M, Kenney E, Eleftherianos I, O'Halloran D, Hawdon J M (2017) Identification of candidate infection genes from the model entomopathogenic nematode *Heterorhabditis bacteriophora*. BMC Genomics, 18:8.

The invention claimed is:

1. Entomopathogenic nematode *Heterorhabditis bacteriophora*, comprising:
  at least one locus, conferring enhanced longevity, from the group consisting of:
  a first locus comprising a single nucleotide polymorphism at position 75 of the nucleotide sequence SC00004647 as depicted in SEQ ID NO: 5, in which C is substituted by T; and
  a second locus comprising a single nucleotide polymorphism at position 54 of the nucleotide sequence SC00006203 as depicted in SEQ ID NO: 7, in which C is substituted by T; and
  at least one locus, conferring an enhanced virulence, from the group consisting of:
  a single nucleotide polymorphism at position 73 of the nucleotide sequence SC00004554 as depicted in SEQ ID NO:3, in which G is substituted by A; and
  a single nucleotide polymorphism at position 111 of the nucleotide sequence SC0010093 as depicted in SEQ ID NO:8, in which G is substituted by A, wherein the nematode is not exclusively obtained by an essentially biological process.

2. Entomopathogenic nematode according to claim 1, having
  a third locus comprising a single nucleotide polymorphism at position 66 of the nucleotide sequence SC00003427 as depicted in SEQ ID NO: 1, in which T is substituted by G; and/or
  a fourth locus comprising a single nucleotide polymorphism at position 76 of the nucleotide sequence SC00004141 as depicted in SEQ ID NO: 2, in which A is substituted by T; and/or
  a fifth locus comprising a single nucleotide polymorphism at position 86 of the nucleotide sequence SC00004634 as depicted in SEQ ID NO: 4, in which C is substituted by T; and/or
  a sixth locus comprising a single nucleotide polymorphism at position 98 of the nucleotide sequence SC00005330 as depicted in SEQ ID NO: 6, in which G is substituted by A; and/or
  a seventh locus comprising a single nucleotide polymorphism at position 77 of the nucleotide sequence SC00012917 as depicted in SEQ ID NO:9, in which C is substituted by G; and/or
  an eighth locus comprising a single nucleotide polymorphism at position 200 of the nucleotide sequence EN-Hb_oxid-11688 as depicted in SEQ ID NO: 10, in which C is substituted by G; and/or
  a ninth locus comprising a single nucleotide polymorphism at position 176 of the nucleotide sequence EN-Hb_oxid-26008 as depicted in SEQ ID NO: 11, in which A is substituted by G.

3. Entomopathogenic nematode according to claim 1, further comprising a thirteenth locus conferring an enhanced virulence, comprising a single nucleotide polymorphism at position 111 of the nucleotide sequence SC00010093 as depicted in SEQ ID NO: 8, in which G is substituted by A.

4. Biological control agent comprising the entomopathogenic nematode according to claim 1.

5. Biological control agent according to claim 4 comprising at least one agriculturally acceptable carrier.

6. A method of controlling insects comprising employing the entomopathogenic nematode according to claim 1 against true weevils (Curculionidae), scarabs (Scarabaeidae) or leaf beetles (Chrsysomelidae).

7. The method according to claim 6 employing the entomopathogenic nematode against the western corn rootworm (*Diabrotica virgifera virgifera*).

* * * * *